US010010686B2

(12) United States Patent
Ambrosina et al.

(10) Patent No.: US 10,010,686 B2
(45) Date of Patent: Jul. 3, 2018

(54) FLUID CONTROL SYSTEM AND DISPOSABLE ASSEMBLY

(71) Applicant: IVENIX, INC., Amesbury, MA (US)

(72) Inventors: Jesse E. Ambrosina, Topsfield, MA (US); Benjamin G. Powers, Portsmouth, NH (US)

(73) Assignee: Ivenix, Inc., Amesbury, MA (US)

( * ) Notice: Subject to any disclaimer, the term of this patent is extended or adjusted under 35 U.S.C. 154(b) by 0 days.

(21) Appl. No.: 14/167,067

(22) Filed: Jan. 29, 2014

(65) Prior Publication Data
US 2014/0148757 A1    May 29, 2014

Related U.S. Application Data

(63) Continuation-in-part of application No. 12/906,077, filed on Oct. 16, 2010, which is a continuation-in-part
(Continued)

(51) Int. Cl.
*A61M 5/38* (2006.01)
*A61M 5/168* (2006.01)
(Continued)

(52) U.S. Cl.
CPC .......... *A61M 5/38* (2013.01); *A61M 5/14224* (2013.01); *A61M 5/16813* (2013.01);
(Continued)

(58) Field of Classification Search
CPC .... A61M 1/16; A61M 1/1621; A61M 1/1037; A61M 1/1601; A61M 1/3626; A61M 2205/12; A61M 5/1415; A61M 2205/128
See application file for complete search history.

(56) References Cited

U.S. PATENT DOCUMENTS 3,320,382 A    5/1967    Beale
3,946,731 A *  3/1976    Lichtenstein ................ 604/66
(Continued)

FOREIGN PATENT DOCUMENTS

EP    0840098 A2    5/1998
GB    2111196 A     6/1983
(Continued)

OTHER PUBLICATIONS

International Search Report and Written Opinion of the International Searching Authority dated Dec. 4, 2007, received in PCT/US2007/05095.
(Continued)

*Primary Examiner* — Scott Medway
(74) *Attorney, Agent, or Firm* — Chapin IP Law, LLC

(57) ABSTRACT

A system for controlled delivery of medicinal fluid includes a fluid pathway assembly defining a fluid pathway and including means for calculating a first calculated fluid flow rate using gas laws. The fluid pathway assembly has an inline flow sensor element received within the fluid pathway movable in response to fluid flowing in the fluid pathway. A flow control device is removably attached to the fluid pathway assembly and has a sensor for sensing a position of the inline flow sensor element in the fluid pathway, the position of the inline flow sensor element being representative of a second calculated fluid flow rate. The fluid pathway assembly includes a variable flow resistor adjustable to regulate a rate of fluid flow in the fluid pathway assembly. A drive mechanism attached to the flow control device is operably coupled to the variable flow resistor when the flow control device is attached to the fluid pathway assembly. The variable flow resistor is adjustable by the drive mechanism to achieve a target flow rate when the first
(Continued)

calculated flow rate and/or the second calculated flow rate differs from the target flow rate.

48 Claims, 18 Drawing Sheets

Related U.S. Application Data of application No. 12/280,894, filed as application No. PCT/US2007/004945 on Feb. 27, 2007, now abandoned, said application No. 12/906,077 is a continuation-in-part of application No. 12/280,869, filed as application No. PCT/US2007/002039 on Jan. 23, 2007, now abandoned.

(60) Provisional application No. 61/904,812, filed on Nov. 15, 2013, provisional application No. 60/777,193, filed on Feb. 27, 2006.

(51) Int. Cl.
*A61M 5/142* (2006.01)
*A61M 5/14* (2006.01)
*A61M 5/145* (2006.01)

(52) U.S. Cl.
CPC ....... *A61M 5/1415* (2013.01); *A61M 5/14593* (2013.01); *A61M 5/16809* (2013.01); *A61M 5/16827* (2013.01)

(56) References Cited

U.S. PATENT DOCUMENTS

| | | | |
|---|---|---|---|
| 4,051,431 A | 9/1977 | Wurster | |
| 4,090,514 A | 5/1978 | Hinck et al. | |
| 4,191,184 A | 3/1980 | Carlisle | |
| 4,300,552 A * | 11/1981 | Cannon | 604/65 |
| 4,358,947 A | 11/1982 | Greene et al. | |
| 4,398,428 A | 8/1983 | Kato | |
| 4,440,239 A | 4/1984 | Evans | |
| 4,470,758 A | 9/1984 | Pazemenas et al. | |
| 4,486,190 A * | 12/1984 | Reinicke | A61M 5/14276 604/67 |
| 4,539,005 A | 9/1985 | Greenblatt | |
| 4,561,298 A | 12/1985 | Pond | |
| 4,634,434 A * | 1/1987 | Marino, Jr. | A61M 5/16881 138/46 |
| 4,714,462 A | 12/1987 | DiDomenico | |
| 4,718,896 A | 1/1988 | Kamen | |
| 4,976,162 A | 12/1990 | Kamen | |
| 5,069,668 A * | 12/1991 | Boydman | A61M 5/172 604/121 |
| 5,176,631 A | 1/1993 | Koenig | |
| 5,207,645 A | 5/1993 | Ross et al. | |
| 5,308,333 A | 5/1994 | Skakoon | |
| 5,308,335 A | 5/1994 | Ross | |
| 5,318,515 A * | 6/1994 | Wilk | A61M 39/28 604/186 |
| 5,324,422 A * | 6/1994 | Colleran | A61M 1/28 210/143 |
| 5,348,539 A | 9/1994 | Herskowitz | |
| 5,421,208 A | 6/1995 | Packard et al. | |
| 5,433,704 A | 7/1995 | Ross et al. | |
| 5,464,391 A | 11/1995 | DeVale | |
| 5,533,381 A | 7/1996 | Seale | |
| 5,554,123 A | 9/1996 | Herskowitz | |
| 5,562,002 A | 10/1996 | Lalin | |
| 5,584,811 A | 12/1996 | Ross et al. | |
| 5,597,042 A | 1/1997 | Tubel et al. | |
| 5,624,409 A | 4/1997 | Seale | |
| RE35,501 E | 5/1997 | Rose et al. | |
| 5,630,709 A * | 5/1997 | Bar-Cohen | F04B 7/0076 417/322 |
| 5,656,784 A | 8/1997 | Butch | |
| 5,681,284 A | 10/1997 | Herskowitz | |
| 5,743,878 A | 4/1998 | Ross et al. | |
| 5,769,608 A | 6/1998 | Seale | |
| 5,788,674 A | 8/1998 | McWilliams | |
| 5,938,634 A * | 8/1999 | Packard | A61M 1/28 604/29 |
| 6,036,296 A | 3/2000 | Axtell et al. | |
| 6,083,206 A | 7/2000 | Molko | |
| 6,275,284 B1 | 8/2001 | Kiel et al. | |
| 6,398,760 B1 | 6/2002 | Danby | |
| 6,461,323 B2 | 10/2002 | Fowler et al. | |
| 6,464,667 B1 * | 10/2002 | Kamen | A61M 5/16809 604/131 |
| 6,495,366 B1 * | 12/2002 | Briggs | 436/16 |
| 6,599,273 B1 * | 7/2003 | Lopez | A61J 1/20 251/149.1 |
| 6,620,151 B2 * | 9/2003 | Blischak | A61M 5/14276 604/891.1 |
| 6,641,562 B1 | 11/2003 | Peterson | |
| 6,642,999 B2 | 11/2003 | Arndt et al. | |
| 6,685,668 B1 | 2/2004 | Cho et al. | |
| 6,877,713 B1 * | 4/2005 | Gray | A61M 5/14224 251/7 |
| 6,972,000 B2 | 12/2005 | Kappel et al. | |
| 6,981,960 B2 | 1/2006 | Cho et al. | |
| 7,055,366 B2 | 6/2006 | Lewis | |
| 7,225,680 B2 * | 6/2007 | Gustafson et al. | 73/754 |
| 7,255,680 B1 | 8/2007 | Gharib | |
| 7,291,126 B2 * | 11/2007 | Shekalim | A61M 5/1454 604/131 |
| 7,402,154 B2 | 7/2008 | Holst et al. | |
| 7,503,903 B2 | 3/2009 | Carlisle et al. | |
| 7,604,610 B2 * | 10/2009 | Shener | A61M 3/0258 604/65 |
| 7,654,982 B2 | 2/2010 | Carlisle et al. | |
| 7,847,276 B2 * | 12/2010 | Carlisle | A61M 5/16886 250/573 |
| 8,067,760 B2 | 11/2011 | Carlisle et al. | |
| 8,105,265 B2 * | 1/2012 | Demers | A61M 1/106 210/739 |
| 8,197,439 B2 * | 6/2012 | Wang | A61M 1/28 604/67 |
| 8,591,200 B2 * | 11/2013 | Marica | F04B 47/04 417/385 |
| 9,170,267 B2 * | 10/2015 | Kim | G01N 35/1095 |
| 2002/0019714 A1 | 2/2002 | Carlisle et al. | |
| 2003/0130625 A1 | 7/2003 | Jacobson et al. | |
| 2004/0254542 A1 | 12/2004 | Sacco | |
| 2005/0126998 A1 * | 6/2005 | Childers | 210/646 |
| 2005/0131332 A1 * | 6/2005 | Kelly et al. | 604/4.01 |
| 2005/0177111 A1 | 8/2005 | Ozeri et al. | |
| 2005/0235733 A1 | 10/2005 | Holst et al. | |
| 2005/0257595 A1 | 11/2005 | Lewis | |
| 2006/0087325 A1 | 4/2006 | Ariav et al. | |
| 2006/0155236 A1 * | 7/2006 | Gara et al. | 604/4.01 |
| 2007/0156089 A1 * | 7/2007 | Yu | 604/131 |
| 2007/0253463 A1 * | 11/2007 | Perry et al. | 374/208 |
| 2007/0271062 A1 | 11/2007 | Vanderveen et al. | |
| 2009/0099518 A1 | 4/2009 | Mager | |
| 2009/0124963 A1 * | 5/2009 | Hogard et al. | 604/30 |
| 2009/0131863 A1 | 5/2009 | Carlisle et al. | |
| 2010/0063765 A1 | 3/2010 | Carlisle et al. | |
| 2011/0028937 A1 | 2/2011 | Powers et al. | |
| 2011/0218414 A1 | 9/2011 | Kamath et al. | |
| 2013/0201471 A1 | 8/2013 | Bui et al. | |

FOREIGN PATENT DOCUMENTS

| | | |
|---|---|---|
| JP | 06-308144 A | 11/1994 |
| JP | 10-160527 A | 6/1998 |
| JP | 2001-221666 A | 8/2001 |
| WO | WO89/01795 A1 | 3/1989 |
| WO | WO90/13795 A2 | 11/1990 |
| WO | 1996013288 A1 | 5/1996 |
| WO | 2000072900 A1 | 12/2000 |
| WO | WO01/30422 A1 | 5/2001 |
| WO | WO05/82450 A1 | 9/2005 |

(56) References Cited

FOREIGN PATENT DOCUMENTS

| WO | WO2007/098265 A2 | 8/2007 |
| WO | WO2007/098287 A2 | 8/2007 |
| WO | WO2007/106232 A2 | 9/2007 |

OTHER PUBLICATIONS

International Search Report and Written Opinion of the International Searching Authority dated Apr. 1, 2008, received in PCT/US2007/04945.
European Search Report dated Dec. 3, 2009, received in European Patent Application No. 07717007.4.
European Search Report dated Dec. 11, 2009, received in European Patent Application No. 07751685.4.
European Search Report dated Dec. 11, 2009, received in European Patent Application No. 07751828.0.
English language abstract for JP10-160527 (1998).
English language abstract for JP2001-221666 (2001).
International Search Report and Written Opinion of the International Searching Authority dated Sep. 11, 2008, received in PCT/US2007/02039.
English language abstract for JP06-308144 (2006).
International International Preliminary Report on Patentability of the International Preliminary Examining Authority dated Jun. 14, 2010, received in PCT/US2007/04945.
International Search Report, PCT/US2014/065342, dated Feb. 26, 2015, pp. 3.
Extended European Search Report for EP14862238.4; dated Jan. 17, 2017; 9 pages.

\* cited by examiner

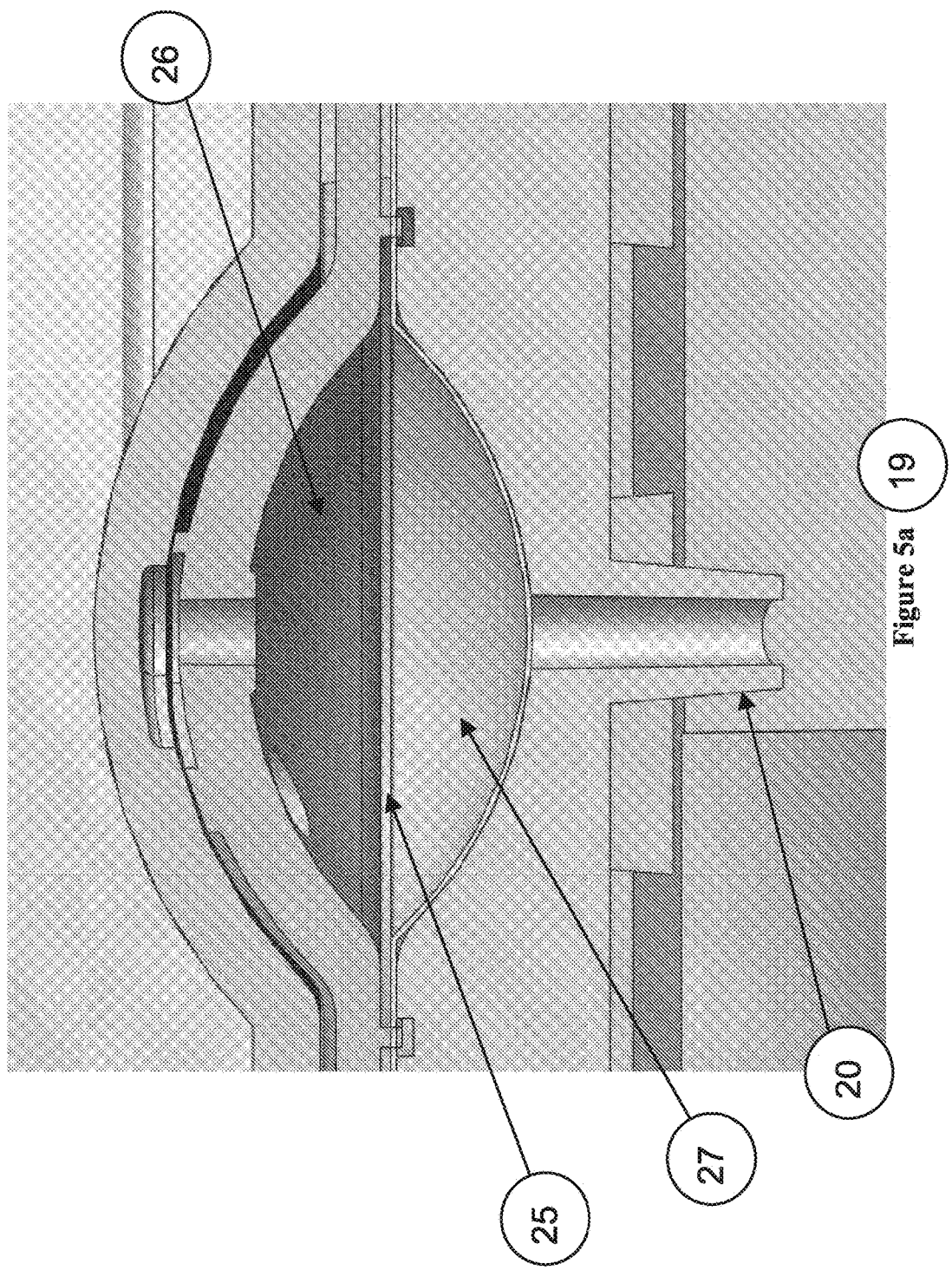

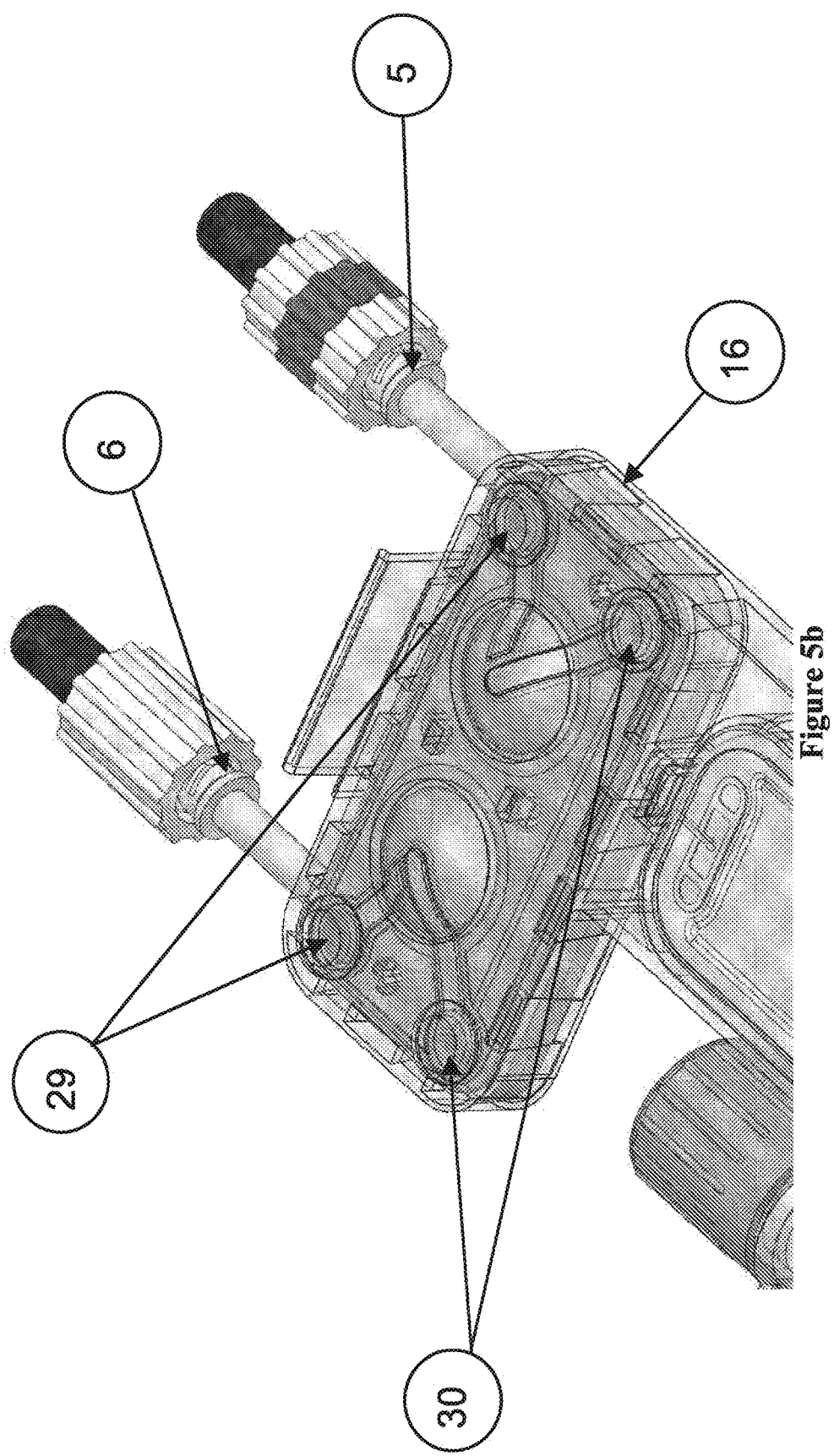

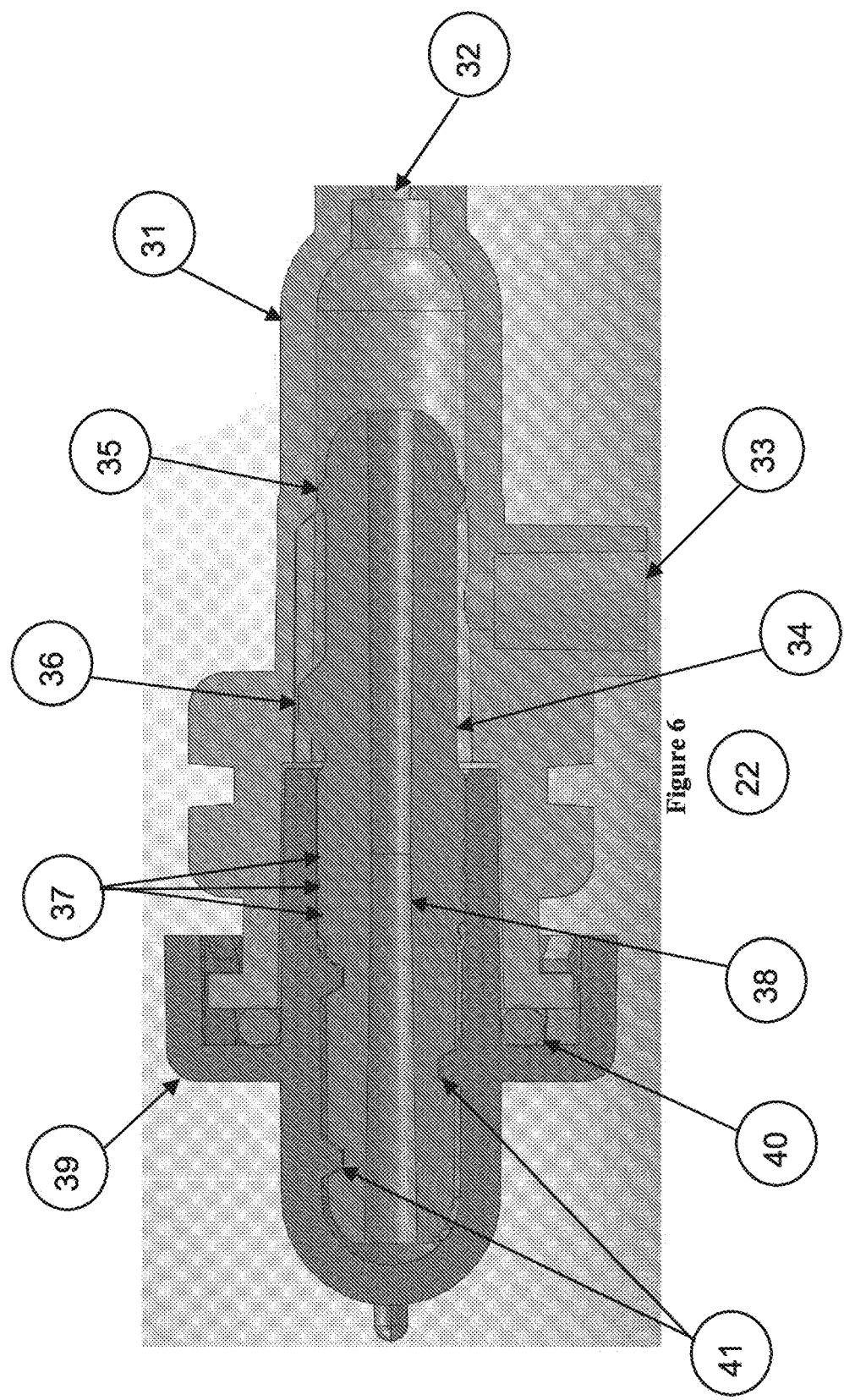

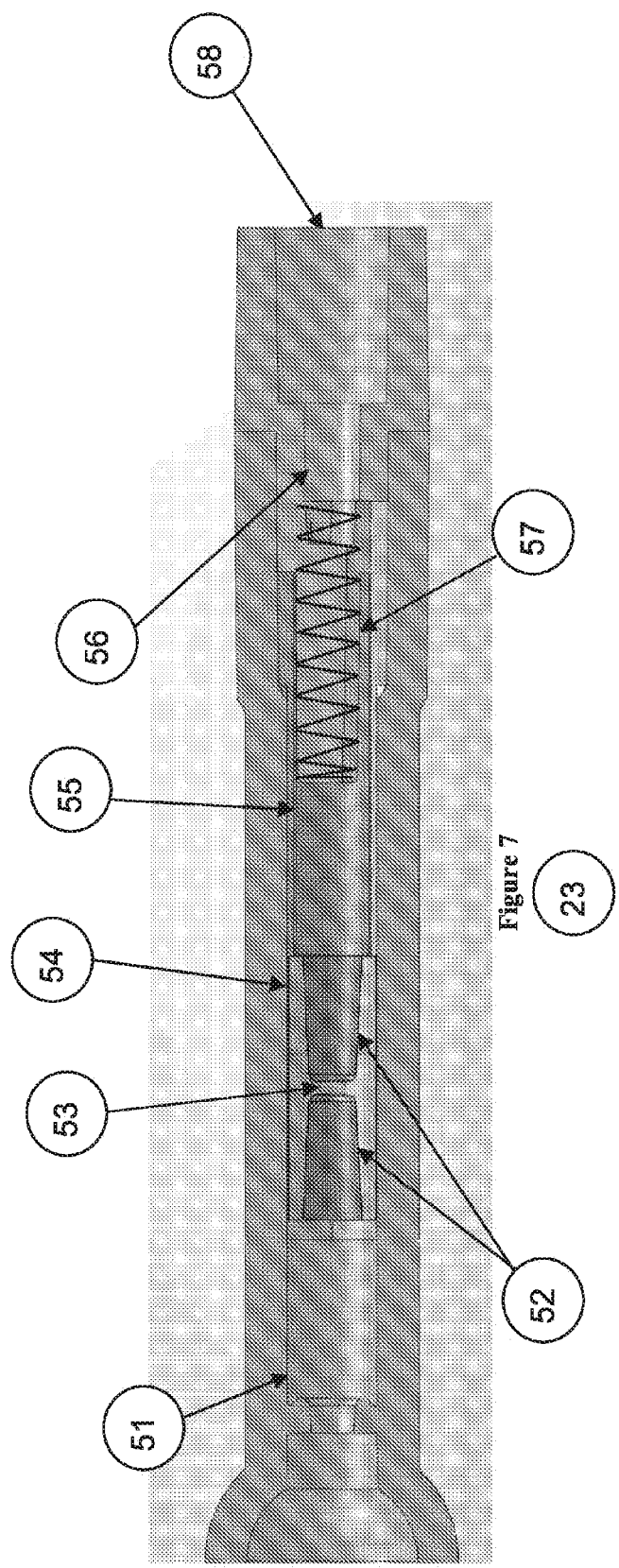

FLUID CONTROL SYSTEM AND DISPOSABLE ASSEMBLY

RELATED APPLICATIONS

This application is related to and claims the benefit of earlier filed U.S. Provisional Patent Application Ser. No. 61/904,812 entitled "SYSTEM AND METHOD TO TOLERATE LARGE AMOUNTS OF AIR DURING AN INFUSION," filed on Nov. 15, 2013, the entire teachings of which are incorporated herein by this reference.

This application is a continuation in part of earlier filed U.S. patent application Ser. No. 12/906,077 entitled "AUTOMATED FLUID FLOW CONTROL SYSTEM," filed on Oct. 16, 2010, the entire teachings of which are incorporated herein by this reference.

U.S. patent application Ser. No. 12/906,077 entitled "AUTOMATED FLUID FLOW CONTROL SYSTEM," filed on Oct. 16, 2010, is a continuation in part of U.S. patent application Ser. No. 12/280,894 filed on Aug. 27, 2008, the entire teachings of which are incorporated herein by this reference.

U.S. patent application Ser. No. 12/280,894 filed on Aug. 27, 2008, is a 371 of United States Patent Application Serial Number PCT/US07/04945 filed on Feb. 27, 2007, the entire teachings of which are incorporated herein by this reference.

United States Patent Application Serial Number PCT/US07/04945 filed on Feb. 27, 2007, claims the benefit of U.S. Provisional Patent Application Ser. No. 60/777,193 filed on Feb. 27, 2006, the entire teachings of which are incorporated herein by this reference.

U.S. patent application Ser. No. 12/906,077 entitled "AUTOMATED FLUID FLOW CONTROL SYSTEM," filed on Oct. 16, 2010, is a continuation in part of U.S. patent application Ser. No. 12/280,869 filed on Aug. 27, 2008, the entire teachings of which are incorporated herein by this reference.

U.S. patent application Ser. No. 12/280,869 filed on Aug. 27, 2008, is a 371 of United States Patent Application Serial Number PCT/US07/02039 filed on Jan. 23, 2007, the entire teachings of which are incorporated herein by this reference.

United States Patent Application Serial Number PCT/US07/02039 filed on Jan. 23, 2007, claims the benefit of U.S. Provisional Patent Application Ser. No. 60/777,193 filed on Feb. 27, 2006, the entire teachings of which are incorporated herein by this reference.

BACKGROUND

The present disclosure relates to intravenous infusion therapy. More specifically, the disclosure relates to a system, components of the system, and methods associated with the system for organizing the fluid flow for applications which require an accommodation of a broad flow rate range, a wide range of input and output pressures, and a wide range of delivered fluid viscosities, such as those seen with Intravenous (IV) infusion therapy.

Conventionally, healthcare providers have had three technical options for intravenous infusions. Many intravenous infusions are controlled by manually adjusting a resistance in the flow path between a fluid source and the patient, based on the operator's observation of the rate of drips formed within a chamber in line with the fluid flow. The flow rate range that can be controlled with this method is limited by the relatively large and fixed size of the drops and the relatively low reliability of the human operator to accurately compute the flow rate. This method is critically flawed by virtue of the fact that it requires a human observer to maintain an accurate and consistent flow rate. In many circumstances, a trained human observer is not available. This manual method also lacks an important ability to electronically record and communicate the results of the infusion.

A relatively small number of infusions are controlled with the use of a fixed volume of liquid under a fixed amount of pressure and a fixed resistance, providing a fixed flow rate. Unfortunately, the fixed rate and fixed fluid volume do not provide the flexibility required for most infusions. Similar to a manual infusion, this method does not provide the opportunity to electronically record the results of the infusion.

Because of the strong requirement for more precise control of flow rate, flexibility of fluid volumes, and the desire to keep track of the flow information, many infusions are controlled using a positive displacement fluid pump. These large volume positive displacement devices are generally of the peristaltic or reciprocating piston type. Both types come at a price of complexity, size, weight, limited battery life, and significant financial cost. Early versions of positive displacement pumps created a new hazard for patients in what was known as "runaway infusion," where the highly controlled fluid flow was suddenly uncontrolled when a door or other containment mechanism on the pump was released. In response to this undesirable feature, pumps were later required to incorporate "flow stop" mechanisms, so that the flow rate would stop entirely if the fluid tubing were removed from the flow control device. Unfortunately, the cessation of flow is sometimes as hazardous to patients as a sudden increase. Another unintended consequence of positive pumping systems is the possibility of infusing lethal amounts of air into a patient. This possibility did not exist with low pressure gravity infusions. As a result, positive displacement pumps have incorporated air detection systems to prevent this hazard, yet these alarm systems are the source of very significant nuisance alarms, resulting in operator inefficiency and patient anxiety.

The present disclosure recognizes the safety advantages inherent in a low pressure infusion, the need to accurately control flow, and the necessity of modern healthcare environments to have infusion data electronically available.

BRIEF DESCRIPTION OF EMBODIMENTS

The disclosure is directed to an medicinal fluid administration apparatus and method for using this apparatus, comprising a fluid pathway assembly and a flow control device wherein fluid flowing through the fluid flow system is controlled via closed loop quasi-static adjustment of in-line pressure based resistance in combination with a low pressure pneumatic pump element. This sensor-based infusion platform (SIP) utilizes wireless communication to a network to maintain device software and dataset integrity, broadcast alarms, and record infusion status information.

These and other features of the disclosure, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this disclosure may be employed in various and numerous embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

FIG. 5a shows a section view of the intermediate pumping chamber;

FIG. 5b shows the check valves and fluid path to the intermediate pumping chambers;

FIG. 6 shows a cross sectional view of the variable resistance device;

FIG. 7 shows a preferred embodiment of the flow sensing element;

DETAILED DESCRIPTION OF EMBODIMENTS

Figure 1A:
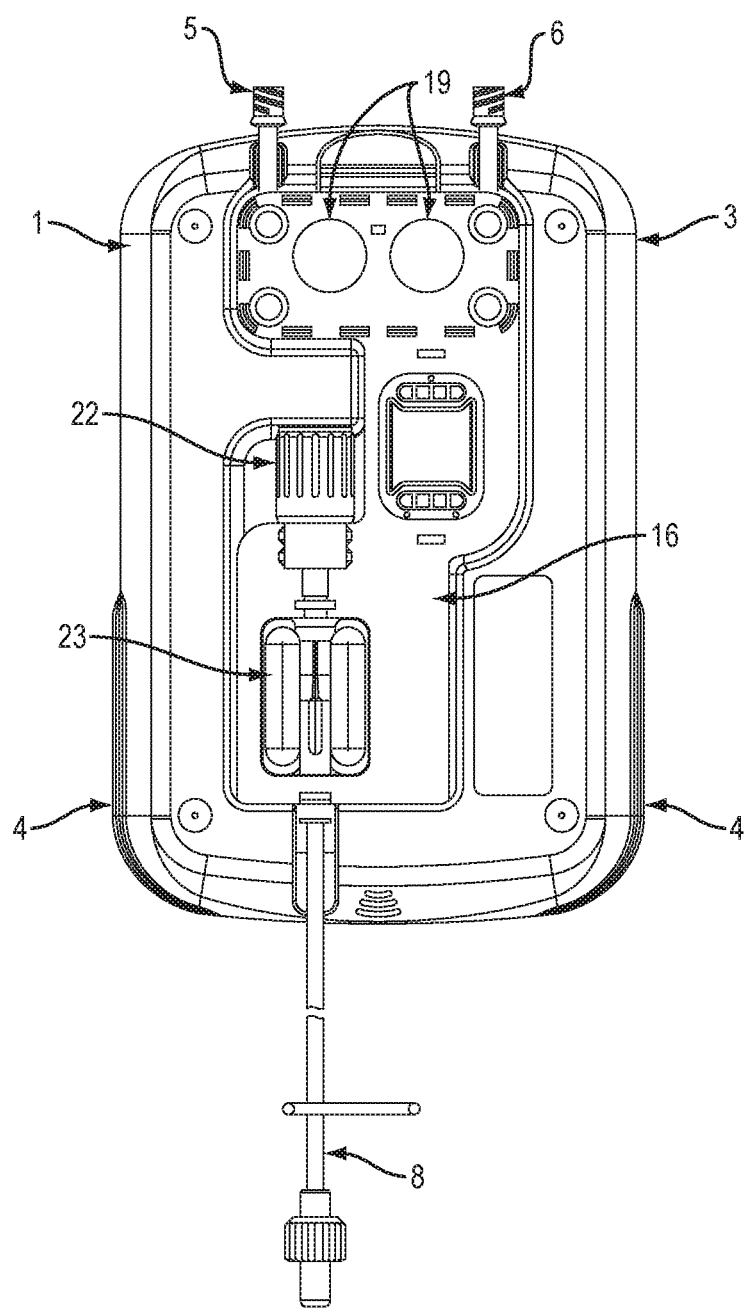
FIG. 1a is a rear view of the preferred embodiment of the Flow Control Device (controller) with the Fluid Path (disposable) installed as would be to deliver an infusion.
Figure 1B:
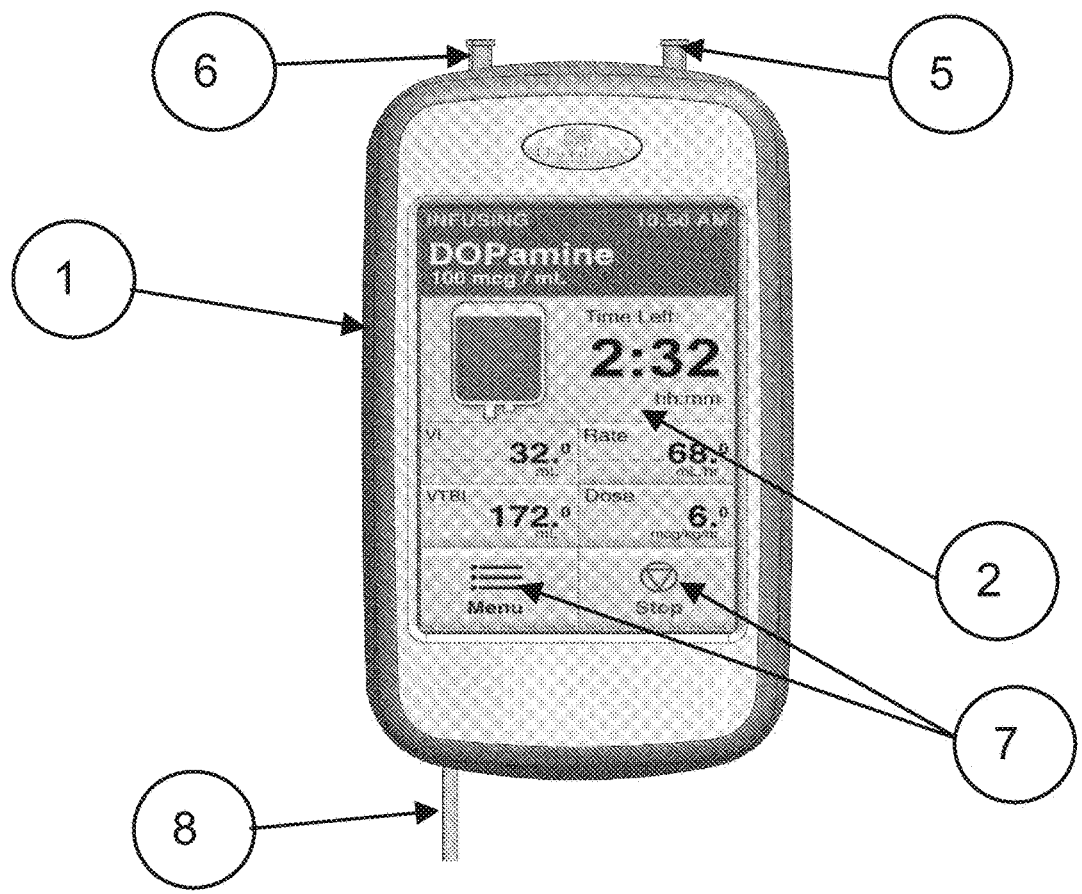
FIG. 1b shows the two major assemblies of the embodiment herein—the Flow Control Device or controller with a Fluid Path (disposable administration set) installed in the pocket in the rear of the of the device.

Referring to the drawings, wherein like reference numerals are used to indicate like or analogous components throughout the several views, FIGS. 1a and 1b depicts an exemplary volume and flow measurement system in accordance with an exemplary embodiment of the present invention. The full sensor based infusion platform system includes a disposable, a controller, an IV pole mounting bar, and a networked computer.

Referring now to FIGS. 1a and 1b, where an exemplary embodiment of the present invention is shown, FIG. 1a is a rear view of the controller with a disposable installed and FIG. 1b shows a front view of the controller with a disposable installed. The controller 1 includes a display 2, which is preferably an LCD display and more preferably a color LCD display with a touch-sensitive input device, such as a capacitive or resistive touch screen overlay 107 (see FIG. 3). Alternative user input devices are also contemplated, such as a keypad or keyboard, mouse, trackball, touchpad, joystick, or combinations thereof as would be understood by persons skilled in the art.

The display 2 is housed in a case or housing 3, e.g., formed of rigid plastic. The controller includes an interface 4 to the pole mount device 60 (see FIG. 9), which both mechanically secures the controller 1 to the IV pole 62 (see FIG. 9). The pole mount 60 may also include a charger for charging the internal batteries or battery pack in the controller, e.g., via charging contacts which are aligned with and electrically couple charging contacts on the controller, or alternatively via induction, when the controller is placed in the mount. Preferably, the charger can charge the internal batteries on either side of the device. The case 3 may include ergonomically designed finger grips or recesses around the circumference to facilitate gripping of the device and may further include a pliable insert either removably or permanently attached to the outer housing 3, for example, via over-molding, co-molding, or otherwise attaching a flexible or resilient material over the rigid shell 3 to further enhance the grip ability of the device.

The inlets 5 and 6 and outlet 8 tube of the disposable are also visible in FIG. 1b. The primary inlet 5 connects the primary fluid source (not shown) containing a volume of fluid to be delivered to the device through a standard luer fitting as is known in the art. Fluid travels through the cassette housed in the rear of the device and then flows to the patient connection through the outlet 8.

The secondary inlet 6 allows a second fluid to be connected to a device independently of and without affecting the current infusion, and then the user can program the device with the second fluid delivery parameters, including start time. At the secondary infusion programmed start time, the controller 1 will temporarily pause delivery of the primary infusion, deliver the secondary infusion per the programmed parameters, and then resume the primary infusion. Other infusion devices on the market require the user to physically hang the second fluid source higher than the first fluid source such that the static pressure of the higher source determines which fluid is delivered. When the hydrostatic head height of second fluid source is not sufficiently higher than that of the primary source, the pump will deliver a mix of both primary and secondary fluids depending on the relative static pressures of the sources, thus not delivering the secondary fluid at the rate—and therefore not delivering the secondary fluid at the desired effective dose—prescribed. This issue, i.e., dependence on the user to manipulate both primary and secondary bag heights, is overcome with this disclosure, as the preferred embodiment will deliver the secondary infusion as programmed independent of the static pressure of the fluid sources.

Features of the disposable administration set ("disposable") 16, and specifically, the cassette portion of the disposable can be seen in FIG. 1a, including the variable flow resistor 22, the flow sensor 23, the flow sensor 23, and the intermediate pumping chambers 19. The variable flow resistor 22 can be automatically adjusted by the controller to match the sensed flow rate with the program flow rate. The flow sensor 23 includes a flow element in the fluid path that moves in response to flow rate and provides the system with both a signal representative of flow rate, but also has a unique signal when air is passing through the sensor. The intermediate pumping chambers 19 pneumatically couple to the controller and act as both pneumatic pumps and additional flow sensors.

FIG. 1b shows the touch-screen display 2 which displays a graphical user interface that is divided into several sections. These sections include information and status displays, status displays that include virtual navigation buttons, and navigation buttons 7. Color and shading of the user interface intuitively show the user where more information is available. The user can touch an onscreen object such as an icon or button to navigate to pages (e.g., which may be arranged in a hierarchical fashion) with more information and change or update the program parameters if needed.

Figure 2:
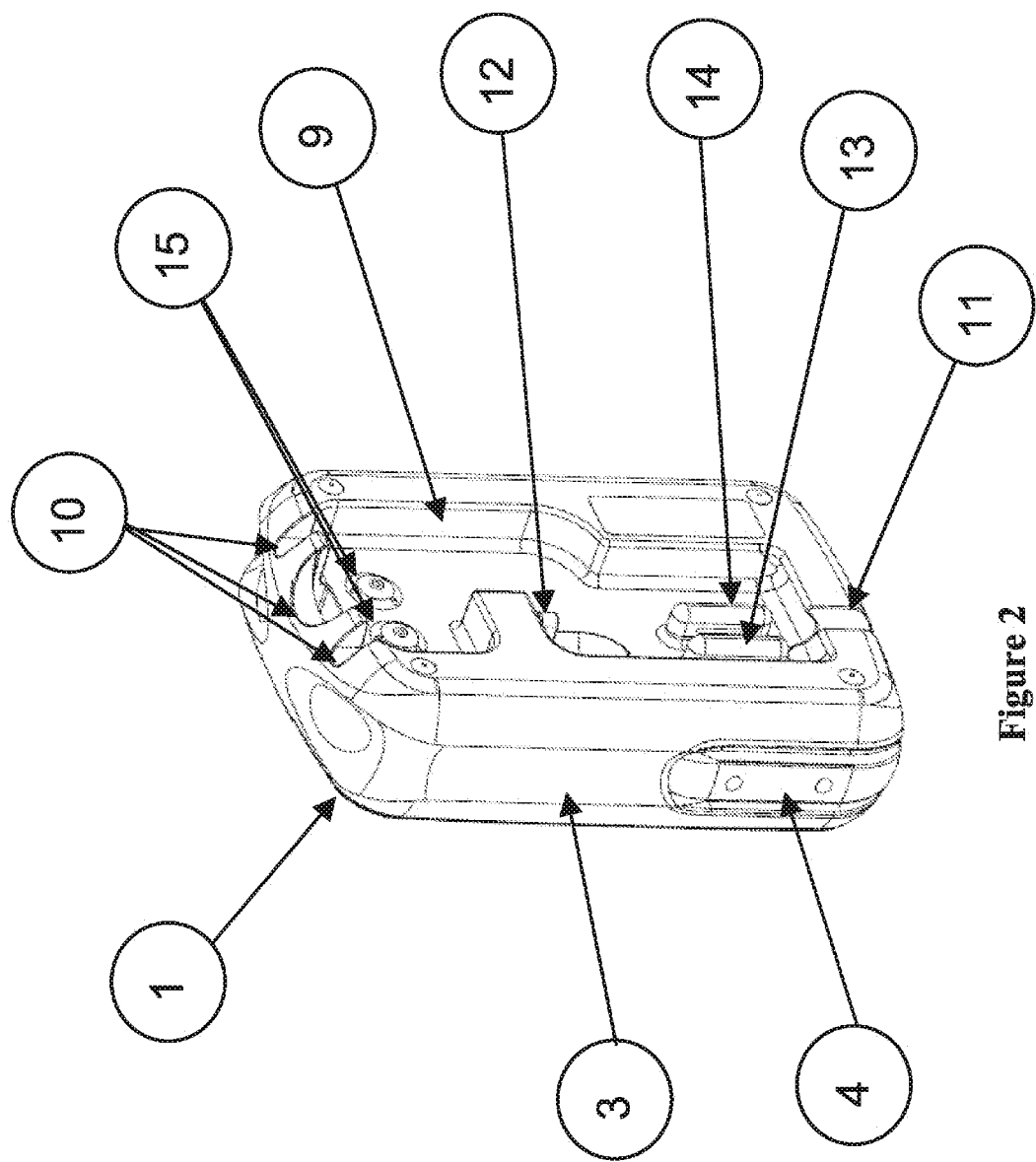
FIG. 2 is a rear perspective view of the flow control device showing the interface to the cassette.

Referring now to FIG. 2, the controller 1 is shown generally from the back and side, where the interface to the disposable is visible. The rear housing 9 is configured to guide the user in proper placement of the disposable into the controller. The asymmetric recess in the rear housing 9 together with recesses 10, 11 provided to allow passage of the primary and secondary inlets 5, 6 and the outlet tube 8, respectively, are three of several features that key the disposable to the controller, thereby preventing the disposable 16 from being installed incorrectly. A rib or spline 12 interlocks with and manipulates the variable flow resistor and is positioned to only allow insertion of a disposable only when the resistor is in the fully closed position (thus preventing uncontrolled flow). Once engaged, the spline 12 does not allow the disposable to be removed from the controller without again fully closing the variable flow resistor.

The light source array 13 and the optical detector 14 are positioned to allow the movable flow element in the disposable to be located between them. When in use, the light source array 13 can preferentially illuminate specific segments of the array, e.g., based on the anticipated location of the flow element, thus enhancing the ability of the optical detector 14 to accurately sense the location of the flow element and saving power to maximize battery run time. The pneumatic interface 15 to the intermediate pumping chambers (IPC's) of the disposables include o-ring seals which help both guide the nipple on the disposable and seal the connection.

Figure 3:
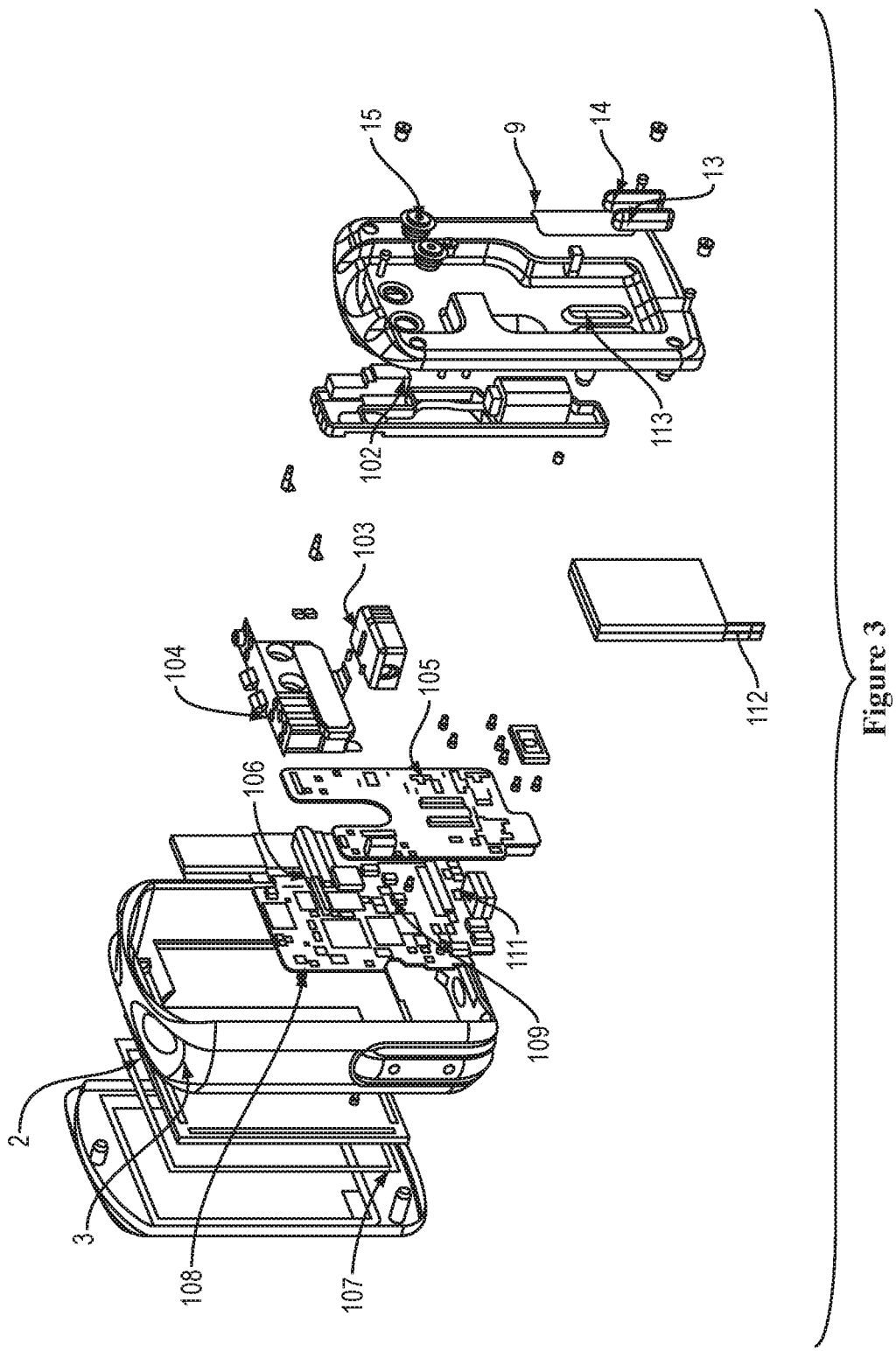
FIG. 3 shows an exploded view of the controller.

Referring now to FIG. 3, where more details of the controller 1 architecture can be seen, the pneumatic interface 15 connects to the manifold 104, housing the valves and sensors, and connecting the pump chamber assembly 102. Pressure sensors in the manifold 104 allow the system to accurately measure pressure in each of the intermediate pumping chambers in the disposable as well as in a calibration chamber of known volume. Isolating the calibration chamber of known volume from the intermediate pumping chambers using the valves in the manifold 104, measuring the pressure present in each chamber, then combining the calibration chamber to an intermediate pumping chamber by opening a valve and measuring the resulting pressure allows the system to calculate the volume of fluid in the intermediate pumping chamber using ideal gas laws. As used herein, the term "ideal gas law" is intended to encompass not only the equation PV=nRT, but also special cases of this law, such as Boyle's Law and Charles' Law. The fluid flow rate is calculated by periodically calculating the volume of fluid entering and leaving the intermediate pumping chambers over time.

The pump chamber assembly 102 includes the pumps and chambers creating a positive pressure source and a negative pressure source. These pressure sources are connected through the manifold 104 to the intermediate pumping chambers of the disposable. As negative pressure is connected to an intermediate pumping chamber, fluid is drawn from the fluid source. As positive pressure is connected to an intermediate pumping chamber, fluid is expelled from the chamber. Controlling the pressures in each of the sources allows the system to compensate for changes in source height and in changes in outlet back pressure. Controlling the timing of the pressure changes allows the system to change the fluid flow rate through the system.

A second means of control of fluid flow through the system is accomplished by the inclusion of a variable flow fluid resistor within the fluid flow path that can be manipulated by the variable resistor drive mechanism 103. The drive mechanism 103 includes a motor and gear mechanism that output torque to a spline 12 (see FIG. 2) that couples with the variable flow resistor on the disposable. As the spline rotates over its 300-degree range of motion, it moves the variable resistor from fully closed to fully open. The resistor is designed to provide a logarithmic response throughout its range of motion, yielding an effective control over a four order of magnitude range (e.g., 0.1-1000 ml/hour) of the system.

The control board assembly 105 including a processor, microprocessor, or the like, and associated electronics executes the fluid delivery programs sent to it by the user interface (UI) board assembly 106. The control board assembly 105 also manages inputs from temperature sensors, an external pressure sensor, the intermediate pump chamber pressure sensors, and the flow sensor; determines and executes changes in pneumatic pressure and resistance settings to match the measured flow rate to the programmed flow rate and sends infusion status updates to the UI board assembly 106. The UI board assembly 106 includes a three axis accelerometer for motion sensing as well as sensors for monitoring the ambient noise level. This data, including the temperature and pressure signals collected and managed on the control board assembly 105, allows the pump to be situationally aware.

The UI board assembly 106 drives the display 2 and manages the user interface, allowing users to program new infusions, change the parameters of existing infusions, and view the history and status of infusions run on the device. The UI board assembly 106 also manages communication with the control board assembly 105 and communications to networked computers. The UI board assembly 106 may include one or more wireless, e.g., radio frequency (RF) or infrared (IR) transceivers, and in the preferred embodiment includes both 802.11 (WIFI) and 802.15 (ZIGBEE) radios 108 and 109, respectively, to enable wireless network communications. Network communication enables the device to send infusion status information to populate electronic medical records, e.g., stored in a network database or remotely located database) and alarm notifications to page the caregiver. Network communications also allows the device to receive updated infusion datasets and software updates.

If the ZIGBEE 109 network is installed in the hospital or other use environment, the device becomes location aware, and the location of the device can be included in all messages. Since location of the device is often associated with a patient, the device can assist the user in identifying the patient to whom the device is attached. Additionally, ZIGBEE networks—because they are mesh networks—allow the software to warn a caregiver if the same medication in the same location is already being given to the same patient. In acute cases, some patients may be connected to up to 12 infusion devices. Devices currently on the market warn the caregiver if the same drug is already being infused only if it is on the same device as the one being programmed, which can lead to poor outcomes for the patient.

The ZIGBEE networked advantage of the preferred embodiment herein is to improve safety by having communication between all devices within a specific location, coordinating infusions and communication to caregivers. A further benefit of a ZIGBEE network is the ability to use ZIGBEE frequency RFID devices on caregivers. When a caregiver walks near a ZIGBEE device with the RFID device, the system recognizes and records that that caregiver is associated with a device. Associating caregivers, patients, and infusions helps provide complete electronic documentation. When a caregiver chooses to program a new infusion, the caregiver selects the drug to be infused, e.g., by viewing it on display 2 and using the touch screen 107 to choose it from a dataset on the device, or by using the controller's bar code imager 111 mounted on the UI board assembly 106 and imaging a bar code, e.g., located on the source of fluid to be infused, through a window in the bottom of the case 3. The bar code imager 111 preferably is of the type that decodes one and two dimensional bar codes and can be used for patient identification, drug identification, drug infusion programming, and caregiver identification. The depicted controller 1 has a dual battery pack 112, providing system redundancy and extended runtime.

Figure 4:
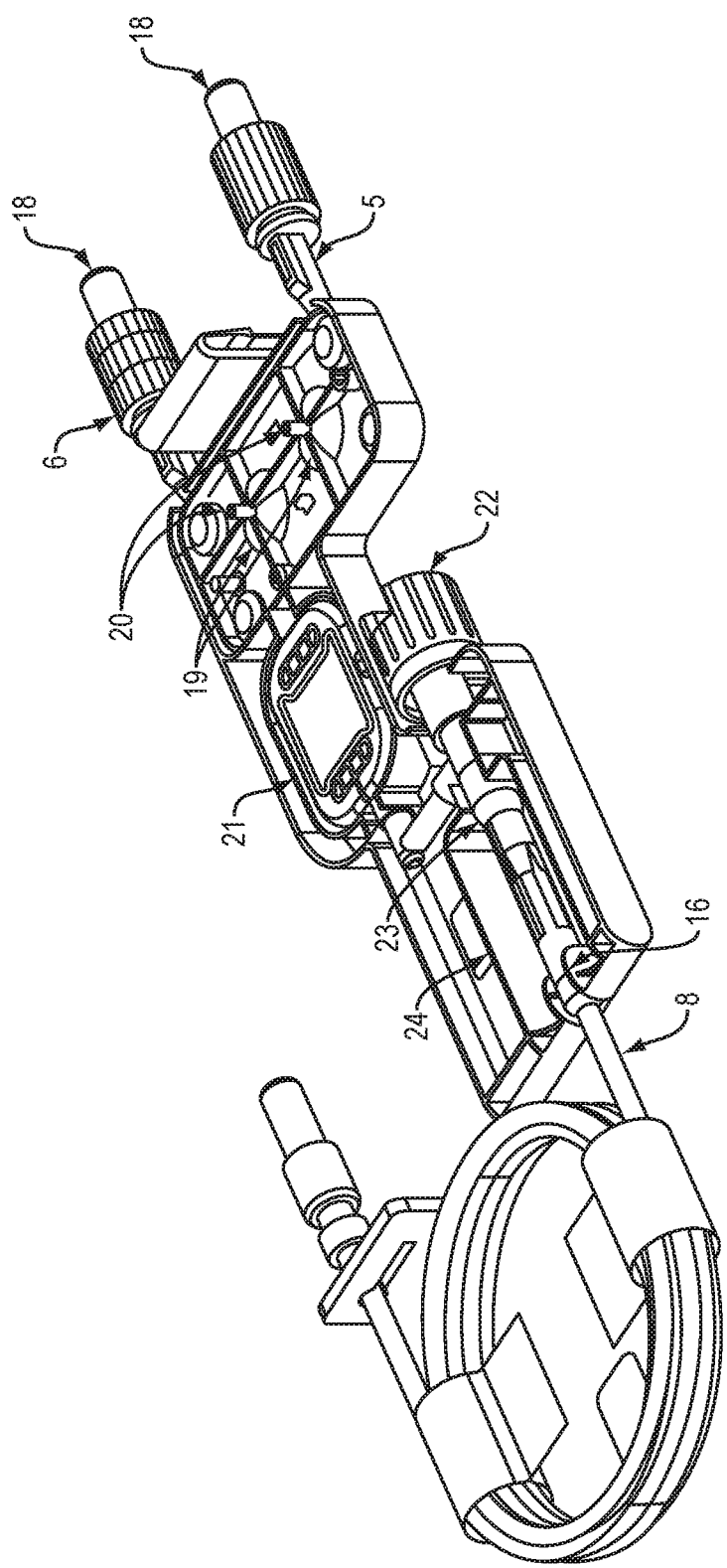
FIG. 4 shows an assembled disposable including a cassette and tubing.

Referring now to FIGS. 4, 5a and 5b, the disposable 16 includes an inlet tube which attaches to the inlet. The disposable 16 may also include a drip chamber and spike (not shown), which can either be used to deliver a gravity infusion, or, in combination with the controller 1, can be used to deliver a sensor based infusion. The disposable 16 has a primary inlet 5 and a secondary inlet 6, both shown with vented caps 18. Fluid from the primary or secondary fluid source flows through the respective inlets 5 or 6 and enters the intermediate pumping chambers 19 through a corresponding one of the one-way or check valves 29. The intermediate pumping chambers 19 are divided by a flexible membrane 25 into two separate volumes 26 and 27.

The fluid entering the chamber flows into volumes 26, and a gas (air) occupies volume 27. The volume 27 that is filled with gas is separated from the fluid in the fluid volume 26 by the flexible membrane 25 and has a port 20 shaped like a nipple, which couples to the pneumatic interface 15 of the controller 1.

When controller 1 applies negative pressure through port 20 to the gas filled volume 27, the flexible membrane moves toward port 20 drawing fluid from the fluid source to fill the chamber. When the controller applies positive pressure through the port 20 to the gas filled volume 27, the flexible membrane is driven from port 20 displacing fluid from the chamber. When all fluid is driven from volume 26, the flexible membrane 25 forms a seal against the fluid outlet of chamber 19. If positive pressure is left in volume 27, the outlet sealed by the membrane 25 will prevent fluid flow when flow is not desired.

Check valves 29 and 30 for each of the primary and secondary flow channels ensure that fluid flows only from the fluid source to the outlet of the disposable 16. The valves 29 prevent fluid in the volume 26 from exiting the volume 26 via the respective inlets 5, 6, e.g., when a positive pressure is applied to the gas volume 27 during operation. Likewise, the valves 30 prevent fluid downstream of the intermediate pumping chamber from being drawn back into the pumping chamber, e.g., when a negative pressure is applied to the gas volume 27 during operation.

Pressure sensors in the controller can determine the pressure in the gas filled volume 27 of the intermediate pumping chamber 19. By sensing the pressure in the gas filled volume and the pressure in a known calibration volume in the manifold 104 and then combining the volumes and measuring the resultant pressure of the combined volumes, the volume of gas in the intermediate pumping chamber can be calculated using the ideal gas law.

If the volume of the rigid IPC is precisely known, it is possible to infer the volume of liquid in the IPC. However, in some instances, e.g., due to manufacturing tolerances variations, it is preferable not to presume that the IPC volume is precisely known and to monitor the flow rate of liquid out of the system using a volume calculation which does not require knowledge of the IPC volume and/or liquid volume. In the preferred embodiment, flow rate is determined by measuring an initial volume of compressible gas in the volume 27 and then monitoring pressure decay in the chamber 27 over time. In reducing the system of the present embodiment to practice, a 500 micro liter combined volume 26 and 27 of the intermediate pumping chambers 19 was selected as being advantageous for both high and low flow rates in that it accommodates the need for flow continuity in the low flow range (e.g.,—less than 1 ml/hour) as well as the need to be able to deliver rapid infusions (e.g., greater than 1000 ml/hour), although other volumes are contemplated.

It can be seen with this design how the system described herein can pause delivery of the primary fluid entering the primary port 5 and being delivered at a primary flow rate, deliver a secondary fluid from the secondary input port 6 at a second flow rate, and then resume delivery of the primary fluid without the need to depend on the user changing the bag heights or otherwise needing to remember to connect, move or otherwise manipulate the primary infusion setup. This arrangement prevents secondary fluid flowing into the primary infusion source, or drawing from both secondary and primary fluid sources at an unknown mix rate, both common occurrences with other systems if the caregiver is not meticulous in system configuration.

Fluids leaving the intermediate pumping chambers 19 flow through an air-elimination filter 21. Many systems in use combine a peristaltic mechanism with a silicone pumping member. Silicone is semi permeable to air and when combined with the high pressures typical of a peristaltic device, air becomes entrained in the fluid being infused. Ultrasonic sensors positioned downstream of the pumping mechanism are employed in those devices to transmit through the tubing of the disposable looking for evidence of air. Those devices have been the source of nuisance (false) alarms and the ensuing wasted time, disposables, and medicinal fluids as caregivers have attempted to remedy constant alarms by changing sets.

This disclosure overcomes those issues by eliminating a high pressure pumping member, which is the root causes of those alarms, instead using low pressure, impervious membranes and incorporation of an air elimination filter. As will be seen, the fluid flow sensor output has a characteristic signature for air and can therefore give an additional layer of safety without an inherent false positive (nuisance) alarm. Fluid passing through the air elimination filter 21 enters the inlet 30 of the variable flow resistor 22.

Referring now to FIG. 6, when the disposable is used for a gravity infusion (i.e., without the use of the controller), the cap 39 can be manually rotated to increase or decrease flow which can be monitored by viewing the drop rate of fluid moving through the drip chamber. In this view, the piston 34 is shown in the fully closed position. As cap 39 is rotated, threads 41 selectively advance or retract the position of the piston 34 within the cavity of flow resistor body 31, depending on the direction of rotation, exposing a helical channel or thread 37 to the incoming fluid, which enters the flow resistor body at inlet 33.

The groove 37 is made with an increasing pitch, width, and/or depth along its length, to selectively increase or decrease the flow area aligned with the inlet of the resistor, the taper of the pitch, width, and/or depth preferably being selected to create a logarithmically increasing flow path for the fluid as the resistor moves from the closed to fully open position. As the thread 37 is exposed to the fluid, fluid travels in the gap created by the threads 37 and cap 39 to flow into the space between cap 39 and piston 34. Fluid in this space exits the flow resistor through a central passage 38 in piston 34 to the outlet 32.

Piston 34 is sealed by an annular ring or protrusion 35 that slides in the cavity of the resistor body 31. Cap 39 is sealed by an O-ring 40. Note that when the cap 39 is rotated, there is no translation of cap 39 with respect to body 31. Rotation of cap 39 translates the piston 34, exposing or hiding different portions of the thread 37 to selectively increase or decrease fluid flow through the device. In contrast to mechanisms used in other systems, such as slide clamps and roller clamps, which when activated send a bolus of drug to the patient, movement of piston 34 does not in itself drive fluid. Therefore, no bolus of fluid to the patient can be created by opening the flow resistor. This unique feature adds yet another layer of safety to the patient and differentiates the device in this preferred embodiment. An exemplary fluid flow resistor may be as described in commonly-owned PCT application No. PCT/US2009/068349 filed Dec. 17, 2009, the entire contents of which are incorporated herein by reference. Fluid exiting variable flow resistor 22 via the outlet 32 enters flow sensor body 23 (see FIG. 7). A protrusion 36 rides in a corresponding groove 42 as the piston 34 is translated to prevent rotation of the piston 34 relative to flow axis.

Referring now to FIG. 7, fluid entering flow sensor body 51 is impeded by sensor element 52, held against the flow opening by spring 57. Sensor element 52 is generally opaque and houses a transparent transmitting element 53, which is transparent (as used herein, the terms transparent and opaque are used in reference to the wavelength of light emitted by the light array 13) and is designed to transmit light onto the sensor array 14. The transmitting element is preferably cylindrical and will be described herein primarily by way of reference thereto, however, it will be recognized that the focusing element 53 may be spherical, cylindrical, or other geometric configuration. An alternative embodiment, which has been contemplated, has a transmission region which is fundamentally spherical and thus focuses the transmitted light onto the sensor. In the alternative embodiment the transmitting element 53 may act a refractive lens, or may be a diffractive and/or holographic optical element for focusing light emitted by the array 13 onto the sensor array 14.

When disposable 16 is in controller 1, flow sensor 23 nests between light source array 13 and optical detector array 14 (see FIG. 2). Light emitted from array 13 is gathered by cylindrical element 53 and focused on detector array 14. As flow increases, sensor element 52 is displaced, compressing spring 57 seated at one end on spring seat 56. The interior flow channel 55 is tapered toward outlet 58 to allow higher flow as more of the tapered area is exposed by the displaced sensor element 52. Ribs 54 maintain sensor element 52 alignment with the central flow axis of the flow path.

There are various alternate embodiments that would be obvious to one skilled in the art, such as the use of a generally cylindrical transparent element in lieu of cylindrical element 53, allowing the transmission of light through the sensor to the detector without focusing the light. As would be understood by one skilled in the art, a sensor of this type when coupled with the light source array 13 and the optical detector 14 would produce unique output signals when measuring the passage of fluid as versus the passage of air. In addition, since air is compressible, bubbles generate a distinct output signal and the flow sensor herein can therefore additionally function as a bubble detector.

Figure 8A:
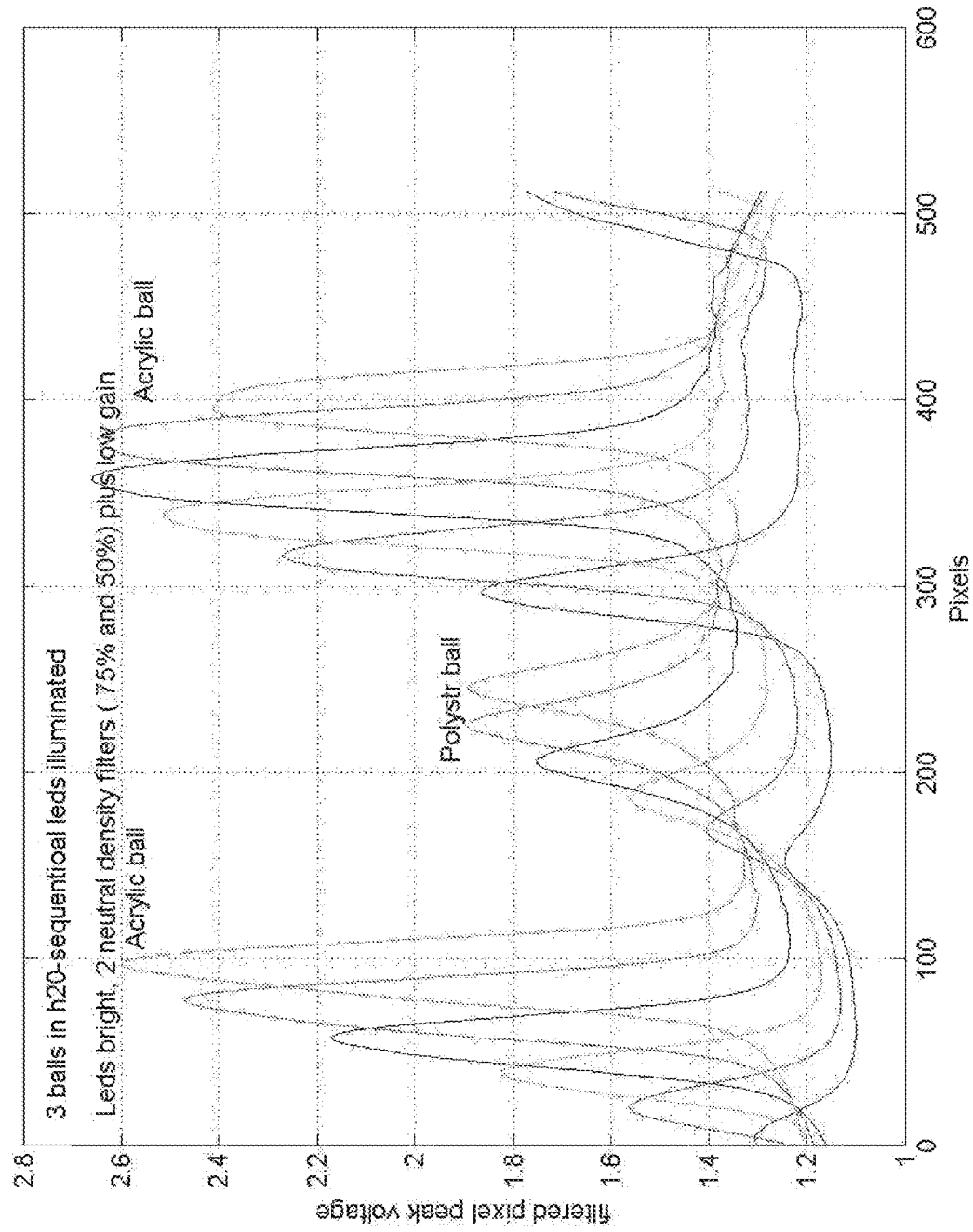
FIG. 8a shows a graph of the sensor output peaks formed when the element focuses and transmits light to the detector.
Figure 8B:
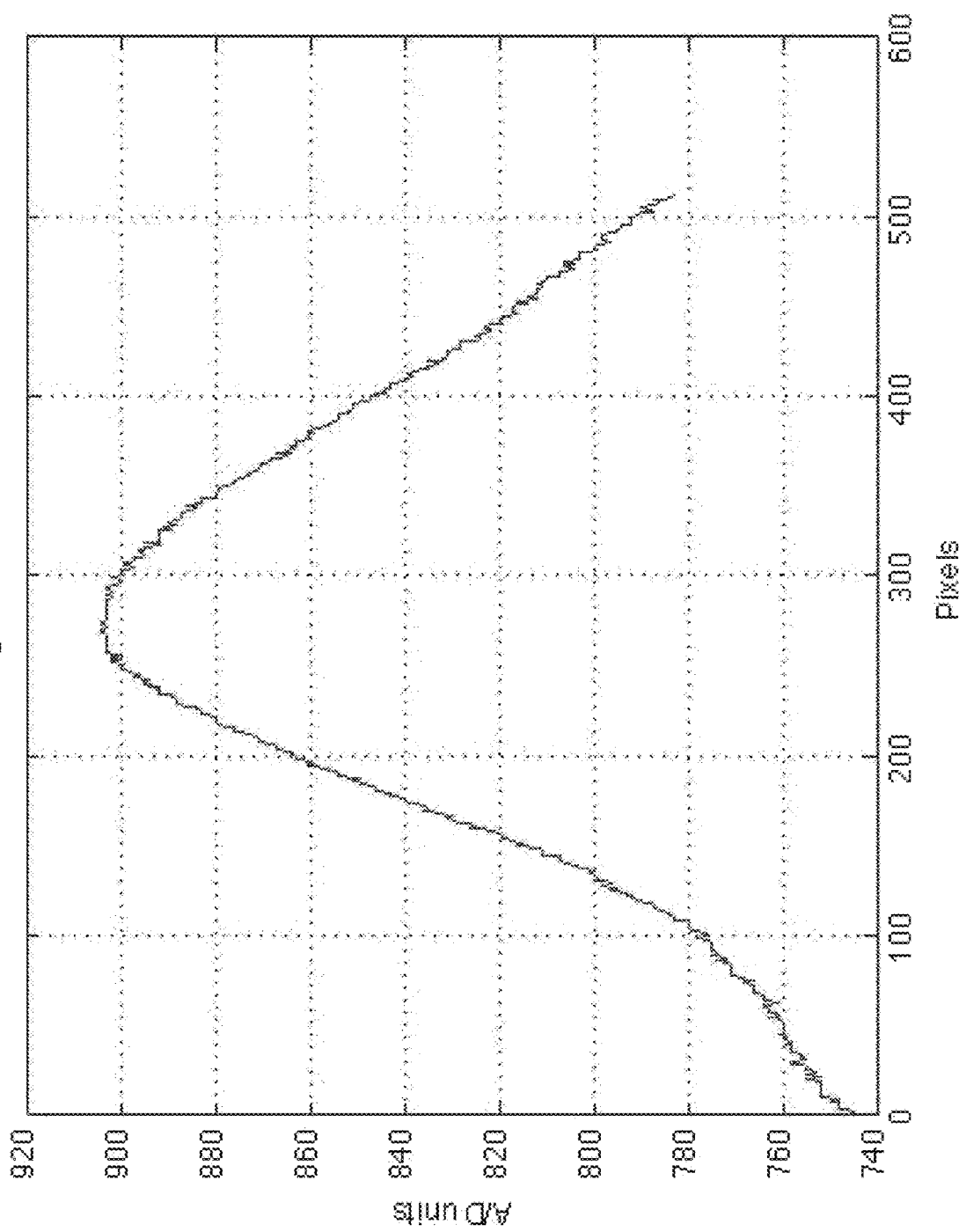
FIG. 8b shows a graph of a sensor output peak with the flow object.
Figure 8C:
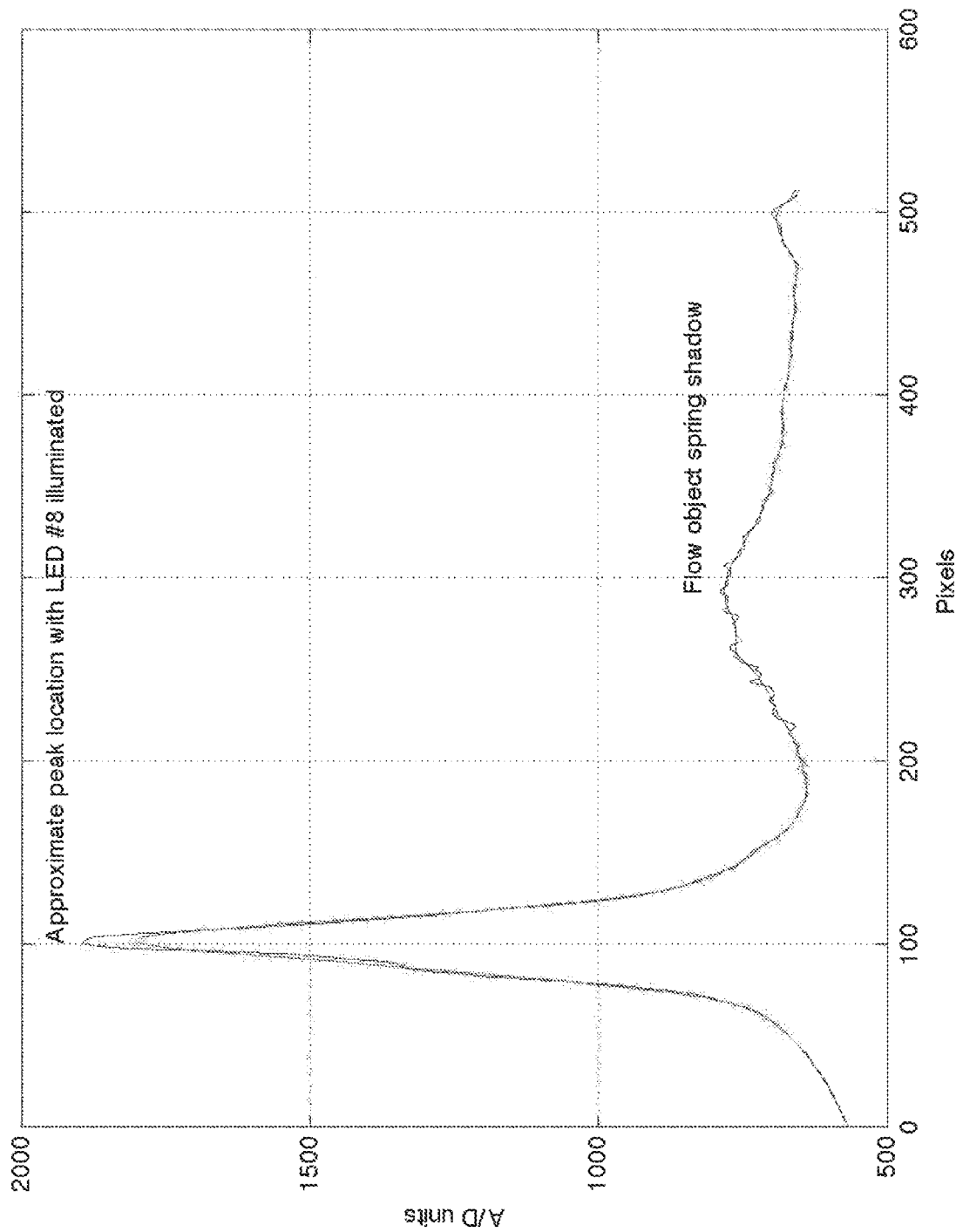
FIG. 8c shows a graph of a sensor output peak with one LED illuminated.

Referring now to FIGS. 8a-8c, it can be seen how significantly the signal voltage is enhanced by using a transparent cylindrical element to transmit light. Referring now to FIG. 8b, a graph is shown with a clear peak of the optical signal of the flow object. A graph showing a clear peak of the optical signal through TPN, a highly scattering fluid, is shown in FIG. 8c.

Referring again to FIG. 4, fluid passing through flow sensor 23 flows through tube 8 to the patient.

Figure 9:
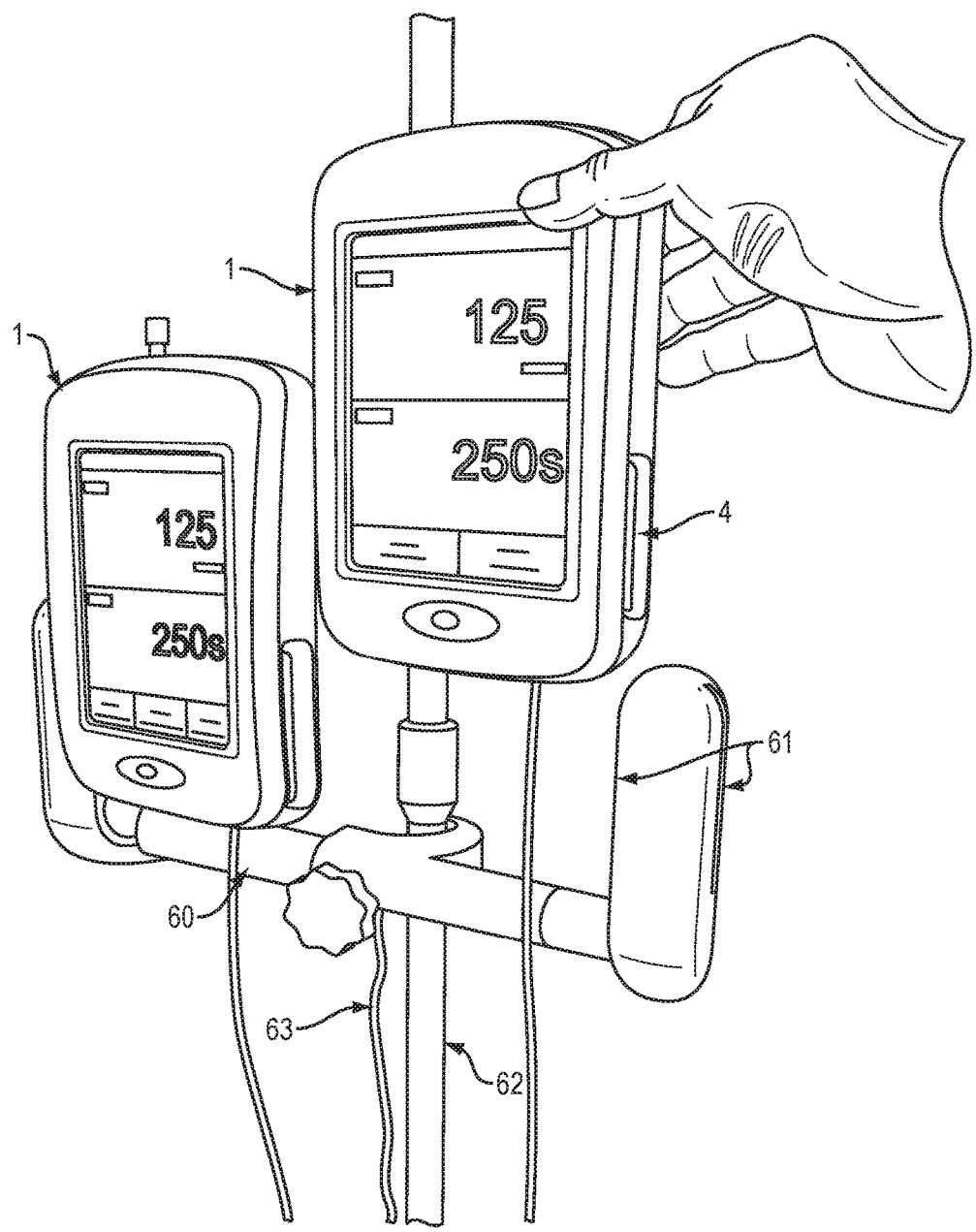
FIG. 9 shows the IV pole bracket mount for the controllers.

Referring now to FIG. 9, controller 1 mounts to pole mount 60 by means of the slide interface 4. Corresponding slides 61 receive controller 1. Low voltage DC electric power provided through cord 63 comes from a transformer connected to a standard AC outlet (not shown) and is transferred through the interface 4 and 61 to charge the batteries 112 of the device. Pole mount 60 can be clamped on any standard IV pole 62 and in the depicted embodiment supports up to four controllers.

A review of adverse infusion events on the FDA's reporting database (MAUDE) shows that a surprising number of adverse events occur each year as a result of a caregiver forgetting to plug the infusion pump back in after the pump or patient is moved. Other devices use only a tiny light or icon to show when the device is plugged in which can easily be missed. Subsequent battery alarms and battery failure can prevent the patient from timely receiving the medication prescribed.

The preferred embodiment of this system addresses this unmet need in two manners: first, pumping air to drive the infusion requires significantly less power than compressing a pumping segment with a peristaltic device, allowing for substantially longer battery life; and the device display will automatically go dark—an additional power savings feature—after a time out from input from a user or from sensed moving if it is not plugged in. The infusion will continue, and the display will periodically come to life, but this new behavior will alert the caregiver that the device is not plugged in and is significantly more prominent and therefore useful than a small indicator light or icon as commonly found on conventional devices.

Another source of adverse events present in other devices but not present in the preferred embodiment of this device is related to occlusions either upstream or downstream that prevent the infusion from proceeding as programmed. There are two associated hazards with other devices on the market with respect to occlusion detection: other devices depend on sensing pressure in the disposable to detect a no-flow condition. Pressure in the disposable will increase over time if there were a downstream occlusion as the pump would continue, filling the compliance available in the disposable until the pressure sensor is able to read sufficient pressure in the line to trip an alarm. When the occlusion is cleared (for example, when the line pinched when the patient was moved is straightened), the pressurized fluid in the line is delivered to the patient as a bolus. This can be a significant hazard as peristaltic pumps can generate high pressure (upwards of 15 psi) which, depending on the compliance of the set and associated delivery catheter and tubing can store and then immediately deliver a significant volume of drug.

The second hazard associated with pressure sensing as a secondary means of sensing fluid flow is that depending on the flow rate, the pressure alarm settings and the compliance of the tube set, the device can run for over two hours without delivering any medication before sufficient pressure builds in the set to trip the alarm. Some courses of therapy depend on a continuous infusion and a two hour interruption can be a significant source of concern. The preferred embodiment of the system disclosed senses flow directly, both with the flow sensor and with the pressure sensors in the intermediate pumping chambers (redundant flow sensing) and therefore is immediately aware of a no-flow condition regardless of the flow rate or the tubing compliance. Secondly, in one non-limiting example embodiment, the pneumatic drive of the system typically operates at one psi, with a maximum of 5 psi available to drive an infusion—a huge improvement in safety as compared to pumps that can deliver fluid in excess of 15 psi. However, these pressures can vary depending on the embodiment.

Finally, the approach of the preferred embodiment allows for a significantly smaller, lighter, and more cost effective approach to accurately delivering an infusion because it does not require a precision mechanism. In instances where previously there had been a tradeoff in infusion delivery and cost, where infusion data, accuracy, and safety were traded off against the cost of delivering that infusion, the preferred embodiment shifts that economic model. In care situations that previously might use cost to drive the use of a gravity infusion or a simpler infusion device, the economics and simplicity of use of this approach allows the infusion to be given at a similar cost, with the advantages of improved safety and traceable electronic data records further reducing the cost of documentation.

Additional Embodiments

Further embodiments herein include a system and method to reduce and/or eliminate delivery of large amounts of air during an infusion of fluid to a recipient. In one non-limiting example embodiment, a fluid delivery system as described herein has the ability to sense and purge large amounts of air introduced from a source container during an intravenous infusion.

The fluid delivery system includes an infusion pump (mechanical infusion pump). The infusion pump can include any suitable resources such as sensors, actuators, control logic, etc., to operate the pump mechanism contained within a disposable tube set. As discussed below, the disposable tube set can include a cassette disposed between multiple tubes. The disposable tube set provides a sterile path from the source fluid container through the pump system to the recipient such as a patient.

Certain portions of this disclosure are based on the observation that the presence of air in the infusion fluid presents a safety risk to the patient. That is, delivery of air along with the infusion fluid to the patient is undesirable because air embolism can cause severe injury or death to the patient. Air can become introduced into a fluid delivery pathway between a fluid source and recipient from many sources. For example, a caregiver can fail to properly purge the disposable tube set during the initial preparation of the treatment; air or other gasses dissolved in the fluid (to be delivered) can come out of solution during the infusion; air can permeate through the walls of the disposable tube set and become entrained in the fluid path; movement of the patient and pump or source container can introduce pockets of air to the pump inlet port; etc.

Another common source of air is the source container containing the fluid that is delivered to a corresponding patient. Typically, source containers are not completely full with liquid (i.e., the container includes some amount of air). In such an instance, if a pump continues to pump fluid from the source container when the source container is empty of liquid, air can be accidentally delivered to the recipient.

In the past, when gravity infusion was the norm, these conditions required vigilant monitoring by the caregiver to avoid harm to the patient. In modern hospitals where automatic infusion pumps are utilized, entrained air is readily detected by an in-line air detection and alarm system in the pump. In general, this detection and alarm system is effective in protecting the patient. However, every time a bubble is detected by the delivery system, the infusion is stopped to prevent injection of air into the patient. To indicate detection of a bubble, an alarm notifies the caregiver that the infusion has been halted and that the delivery system requires immediate attention. Attending to air alarms has become one of the single biggest disruptions to the caregiver's workflow and the patient's comfort.

In contrast to conventional techniques, embodiments herein include a fluid delivery system and corresponding pump mechanism that is able to detect and make appropriate adjustments when large amounts of air are introduced to a pump inlet port. Embodiments herein include a first resource such as an air elimination filter to remove air from fluid being delivered to a corresponding patient. Additionally, downstream from the first resource that eliminates air in the fluid, embodiments herein can include a bubble detector. If the air elimination filter fails, the bubble detector detects presence of bubbles and shuts off a respective pump so that no air is delivered to a corresponding patient. Thus, in contrast to conventional techniques, the bubble detector becomes a backup safety mechanism. In other words, the air elimination filter removes unwanted gas such as air. The bubble detector provides a backup system in case the air elimination filter fails.

The disposable tube set as described herein, including an integrated air vent and integrated measurement and control system in the pump, greatly simplifies the administration of primary and secondary infusion workflows. In addition to the ability to purge small air bubbles in the fluid introduced from gases coming out of solution or diffusing in through the tubing walls, embodiments herein analysis engine able to deal with large amounts of air and take appropriate action.

Figure 10:
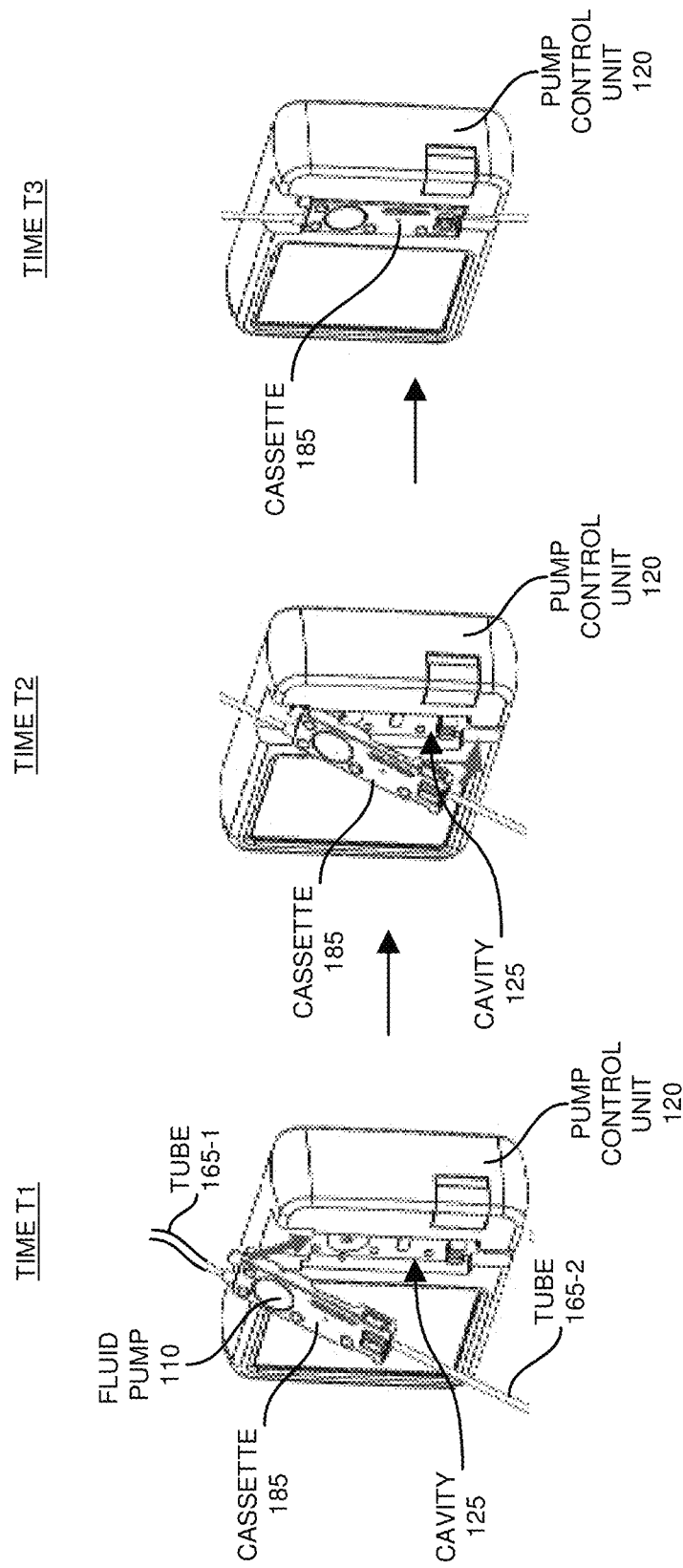
FIG. 10 is an example diagram illustrating insertion of a cassette (disposable) into a corresponding cavity of a pump control unit according to embodiments herein.

Now, more specifically, FIG. 10 is an example diagram illustrating insertion of a corresponding cassette (a.k.a., a disposable as previously discussed) into a cavity the pump control unit according to embodiments herein. In general, the cassette 185 as discussed below facilitates the delivery of fluid received from tube 165-1 through tube 165-2 to a respective patient.

In one embodiment, the fluid pump 110 (a version of which is illustrated in FIG. 5*a*) in the disposable cassette 185 in FIG. 10 has a fluid side and an actuation side separated by a flexible membrane or movable piston. The actuator to control the movable pump chamber 110 in the cassette 185 is contained in the pump controller unit 120. Likewise, the actuators and sensors for the resistor drive, pressure sensor, bubble detector, etc., are contained within the pump controller unit 120. Additional details are discussed in the following figures such as in FIG. 14.

Referring again to FIG. 10, note that all of the actuators and sensors in the pump controller unit 120 can be configured to automatically engage with the respective components in the cassette 185 as the user loads the disposable cassette 185 into the cavity 125 of the pump controller unit 120. For example, the action of pressing the cassette 185 into the pump controller unit 120 ensures all of the mechanisms are seated properly.

In one embodiment, when the pump controller unit 120 is activated, the pump controller unit 120 is able to determine if the cassette 185 is loaded properly into cavity 125. If the pump control unit 120 detects that the cassette 185 is not properly loaded into cavity 125, the pump control unit 120 generates an alert to a caregiver. The alert indicates that corrective action is needed. Alternatively, if the pump control unit 120 detects that the cassette 185 is properly inserted into cavity 125, the pump control unit 120 enables the pump operator to initiate delivery of fluid to a corresponding patient.

As shown in this non-limiting example embodiment, cassette 185 includes tube 165-1 and tube 165-2. A combination of cassette 185 tube 165-1 and tube 165-2 represent a disposable tube set.

Tube 165-1 provides a fluid pathway from a corresponding fluid source (such as medicine) to an input port of the cassette. Tube 165-2 provides a fluid pathway from cassette 185 from an output port of the cassette 185 to a corresponding patient.

As further discussed herein, fluid pump 110 resides between the input port and output the output port of the cassette 185. The pump control unit 120 controls the fluid pump 110 in the cassette 185 to draw fluid through tube 165-1 from a fluid source. The pump controller unit 120 further controls fluid pump 110 to pump the fluid through tube 165-2 to a corresponding recipient.

In this example embodiment, the sequence of frames in FIG. 10 illustrates insertion of the respective cassette into a respective cavity 185 of pump controller unit 120.

At time T1, the operator (such as caregiver) moves cassette 185 towards cavity 125.

At time T2, the operator aligns and inserts an upper portion of cassette 185 into a corresponding location of cavity 125 of the pump control unit 120.

At time T3, the operator completes insertion of the cassette 185 in cavity 125 of the pump control unit 120.

Cassette 185 can be swung or rotated into position after engaging an upper pivot point of cassette 185 into cavity 125.

Note that, alternatively, the pivot point could be at the bottom of the cavity 125. In such an instance, the operator rotates or swings the top of the cassette 185 to complete insertion.

In accordance with yet further embodiments, the cassette 185 and/or cavity 125 in the pump control unit 120 can include hinges. In such an instance, the cassette 185 can be swung (such as from right to left, or left to right) on hinges into the cavity 125.

In accordance with yet further embodiments, loading of the cassette 185 can include merely pushing the cassette 185 into cavity 125 without rotation.

Accordingly, the direction or motion associated with loading of the cassette 185 into cavity 125 can vary depending on the embodiment.

Figure 11:
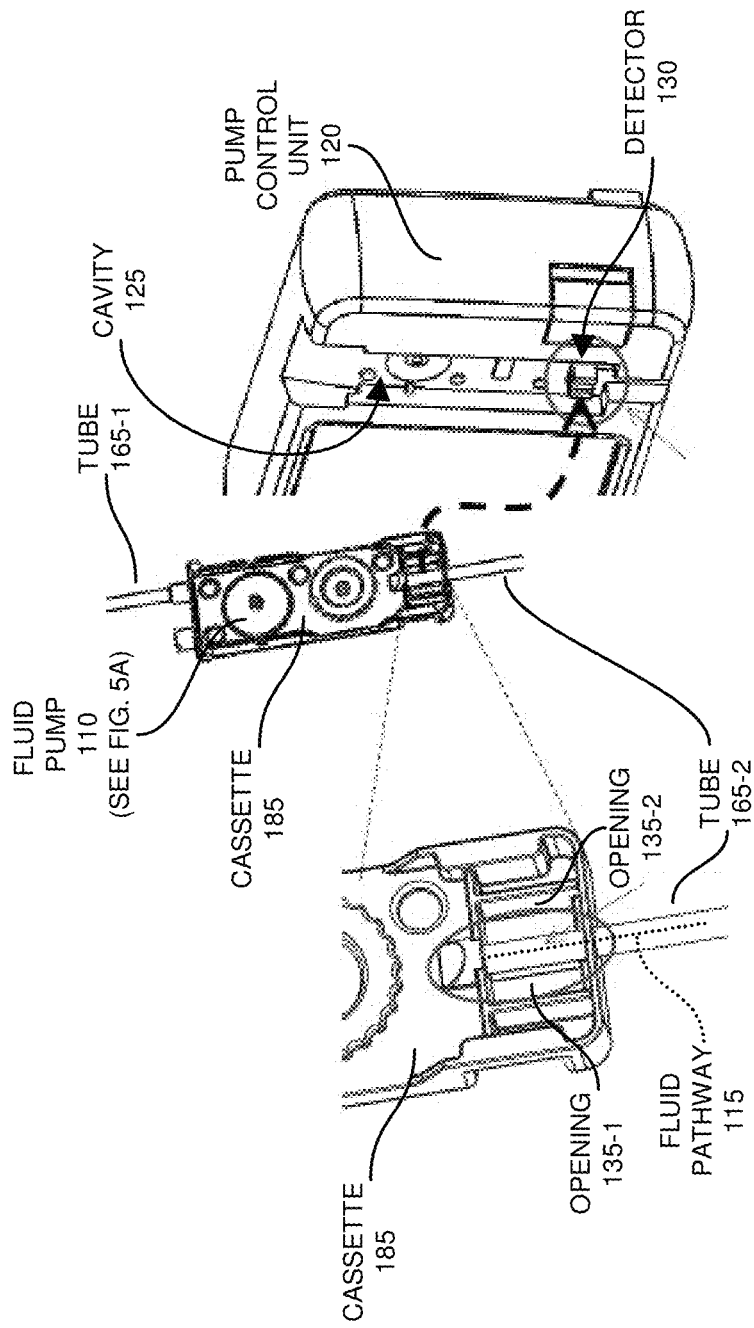
FIG. 11 is an example diagram illustrating alignment of a fluid pathway with a detector disposed in a cavity of a pump control unit according to embodiments herein.

FIG. 11 is an example diagram illustrating additional details of cassette 185 and corresponding cavity 125 according to embodiments herein.

As shown in this example embodiment, cassette 185 includes opening 135-1 and opening 135-2 disposed adjacent to a section of tube 165-2. That is, a portion of tube 165-2 (representing a portion of fluid pathway 115) is disposed between opening 135-1 and 135-2 of cassette 185.

In accordance with one embodiment, insertion of the cassette 185 into the cavity 125: i) aligns and causes a first element of the bubble detector element 130 to pass through and reside in opening 135-1 in the cassette 185, and ii) aligns and causes a second element of the bubble detector element 130-2 to pass through and reside in second opening 135-to of the cassette 185.

After the cassette 185 is inserted into cavity 125 of pump control unit 120, the fluid pathway 115 resides between respective bubble detector elements of detector 130. In other words, in one embodiment, insertion of the cassette 185 in the cavity 125 aligns a portion of the fluid pathway 115 in cassette 185 between a first bubble detector element and a second bubble detector element. In general, bubble detector elements 130 detect presence of bubbles in fluid passing between openings 135-1 and 135-2.

Figure 12:
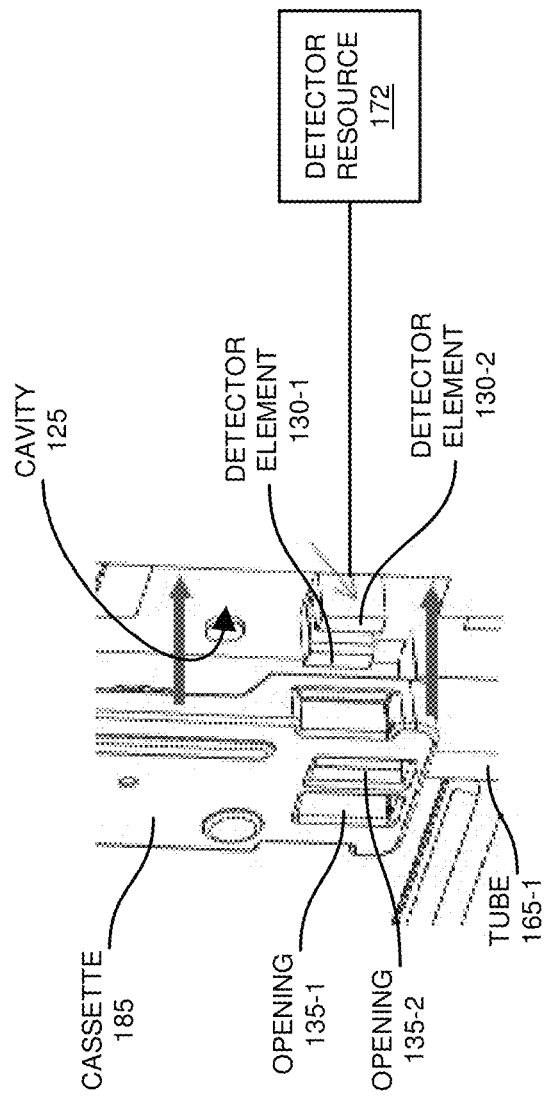
FIG. 12 is an example diagram illustrating passing of bubble detector elements through openings of a corresponding cassette inserted into a cavity of a pump control unit according to embodiments herein.

This is more particularly shown in FIG. 12.

As shown in FIG. 12, cavity 125 of pump controller unit 120 includes bubble detector element 130-1 and bubble detector element 130-2. By way of non-limiting example, each of the bubble detector elements 130-1 and 130-2 can protrude from a surface of the cavity 125 in the pump control unit 120.

As previously discussed, insertion of cassette 185 into cavity 125 causes bubble detector element 130-1 to slide into and eventually reside in opening 135-1. Additionally, insertion of cassette 185 into cavity 125 causes bubble detector element 130-2 to slide into and reside in opening 135-2.

Thus, in one embodiment, insertion of the cassette 185 into the cavity 125 aligns a portion of the fluid pathway 115 in the cassette 185 to be adjacent to one or more bubble detector elements.

In one embodiment, there is a spacing disposed between bubble detector element 130-1 and bubble detector element 130-2 in which a portion of fluid pathway 115 resides. During operation, the bubble detector elements 130 monitor fluid passing through a portion of fluid pathway 115 between or adjacent to detector elements.

Note that inclusion of multiple bubble detector elements 130 shown by way of non-limiting example only. In certain embodiments, only a single bubble detector element disposed adjacent to a portion of fluid pathway 115 is needed to detect presence of bubbles. In such an instance, if desired, cavity 125 may include only a single bubble detector element disposed adjacent to fluid pathway 115 to detect presence of bubbles. The single element can transmit a signal into the passing fluid and then monitor for echoes indicating presence of bubbles. In a case in which multiple elements are deployed, one of the elements can be transmitter the other element can be a receiver.

As further shown in FIG. 12, pump control unit 120 can include bubble detector resource 172 coupled to one or more bubble detector elements 130. During operation such as delivery of fluid to a recipient, upon detection of bubbles for other undesirable matter delivered in fluid to a corresponding recipient, the bubble detector resource 172 notifies controller in pump control unit 120 of the condition.

In one embodiment, in response to detecting presence of bubble or other matter in the fluid being delivered to the recipient as indicated by the detector resource 172, the pump control unit 120 terminates the delivery of fluid and potentially sets off the alarm to notify a corresponding caregiver of the condition. As previously discussed, intravenous delivery of a gas to a patient can be harmful or fatal.

Figure 13:
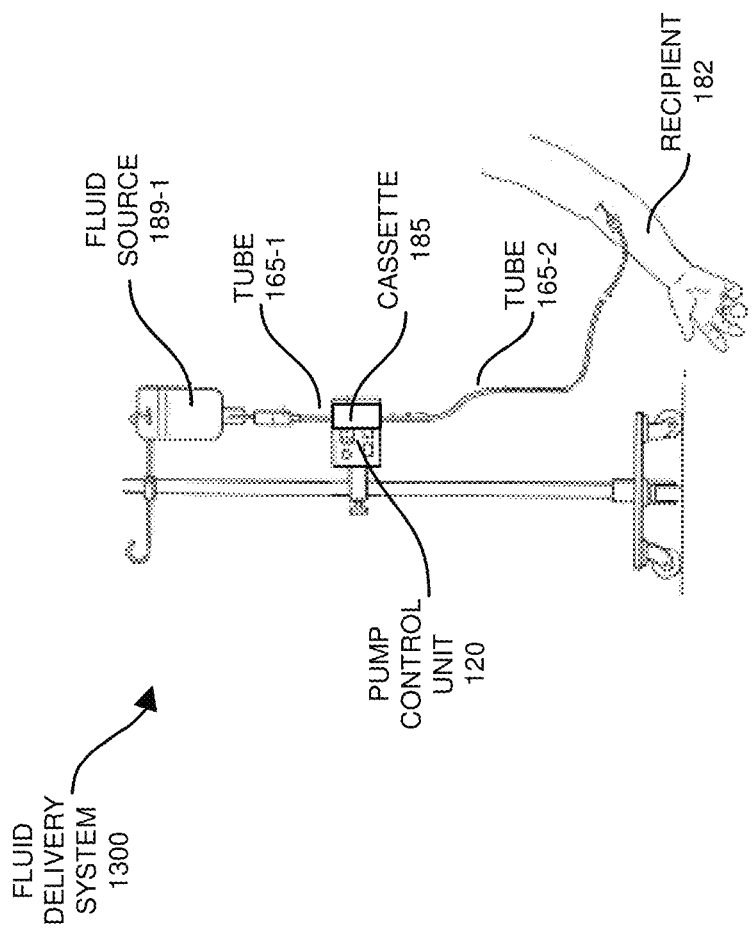
FIG. 13 is an example diagram illustrating use of a pump control unit and corresponding disposable tube set to deliver fluid to a corresponding recipient according to embodiments herein.

FIG. 13 is an example diagram illustrating a fluid delivery system according to embodiments herein.

As shown, the fluid delivery system 1300 includes a fluid source 189-1, pump control unit 120, and disposable tube assembly (such as a combination of cassette 185, tube 165-1, and tube 165-2). In this example embodiment, cassette 185 is already inserted in a corresponding cavity 125 of pump control unit 120.

Pump control unit 120 controls a corresponding pump resource (such as fluid pump 110) in cassette 185 to deliver fluid from fluid source 265 through a fluid pathway through tube 165-1, cassette 185, and tube 165-2 to recipient 182.

Figure 14:
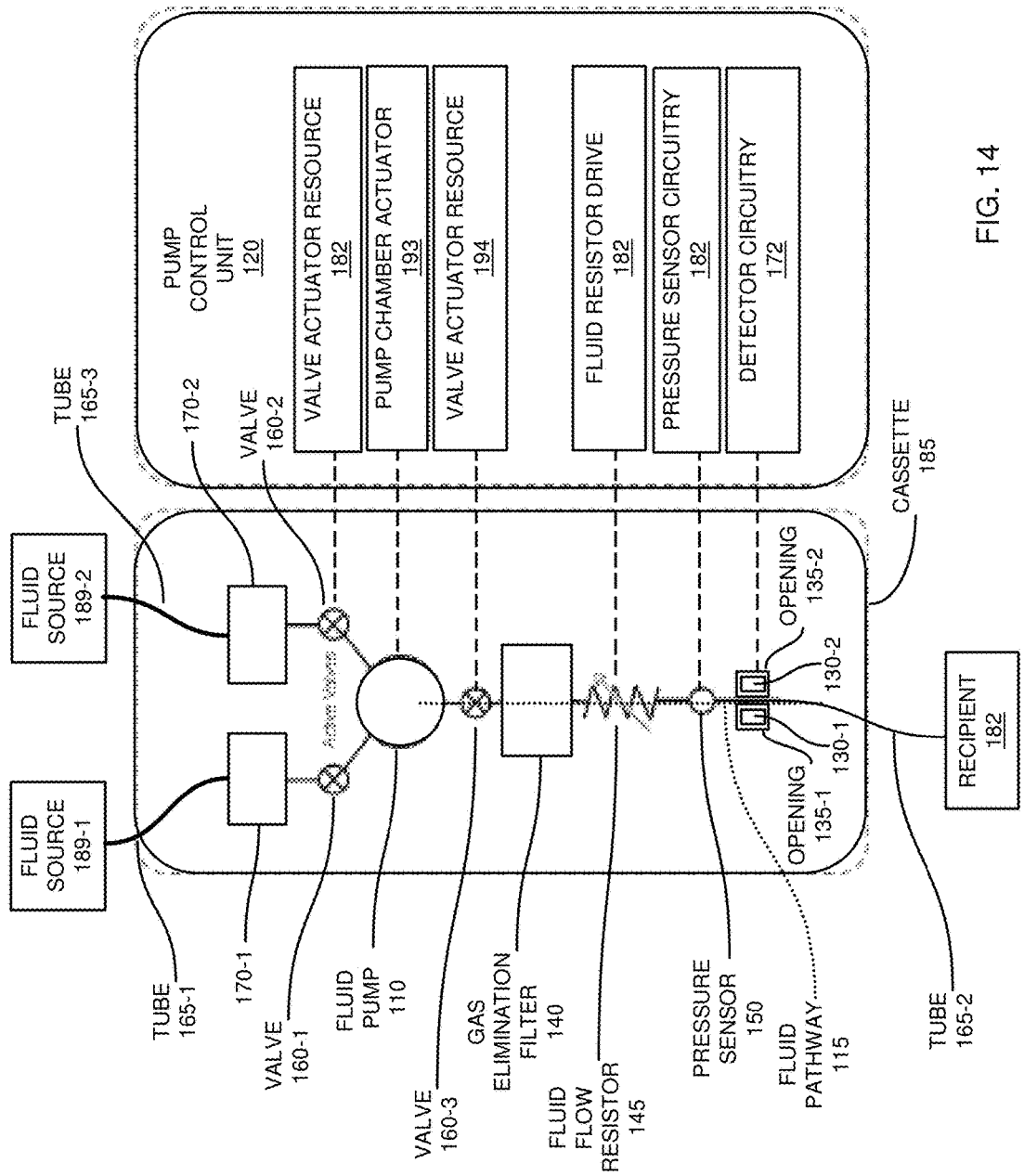
FIG. 14 is an example diagram illustrating details of a disposable tube set and corresponding pump control unit 120 according to embodiments herein.

FIG. 14 is an example diagram illustrating a disposable cassette and corresponding pump control unit according to embodiments herein.

As previously discussed, embodiments herein include cassette 185 that fits into a corresponding cavity 125 of pump control unit 120. In addition to including tube 165-1 and tube 165-2, note that embodiments herein can further include tube 165-3. In one embodiment, a combination of resources including tube 165-1, tube 165-2, tube 165-3, and cassette 185 represent an assembly such as a disposable tube set.

As its name suggests, the disposable tube set can be thrown away after it is used to deliver a corresponding fluid to a patient. The pump controller unit 120 can be used in conjunction with a new disposable tube set to deliver fluid to a next patient. Thus, the pump controller unit 120 is reusable across multiple patients. However, each respective disposable tube set is used on only one patient.

As shown and as previously discussed, insertion of cassette 185 into the corresponding cavity 125 of the pump control unit 120 provides coupling between resources in the cassette 185 and resources in pump control unit 120.

For example, when the cassette 185 is inserted into cavity 125 of the pump control unit 120, valve actuator resource 192 (e.g., valve controllers) become coupled to corresponding valves 160 in the cassette 185. During pump operation, valve actuator resource 192 in the pump control unit 120 controls valves 160-1 and 160-2. Further in this example embodiment, note that valve actuator resource 194 in the pump controller unit 120 controls valve 160-3.

Via control of valve 160-1, the pump control unit 120 is able to control the flow of fluid received from a first fluid source 189-1 through tube 165-1 and primary inlet 170-1 to pump chamber 110. For example, opening valve 160-1 enables a flow of fluid from fluid source 189-1 through tube 165-1 and primary inlet 170-1 into pump chamber 110. Closing valve 160-1 prevents a flow of fluid through the tube 165-1 and primary inlet 170-1 into pump chamber 110.

Via control of valve 160-2, the pump control unit 120 is able to control the flow of fluid received from a second fluid source 189-2 through tube 165-2 and secondary inlet 170-2 to pump chamber 110. For example, opening valve 160-2 enables a flow of fluid through tube 165-2 and secondary inlet 170-2 into pump chamber 110. Closing valve 160-2 prevents a flow of fluid through the tube 165-2 and secondary inlet 170-2 into pump chamber 110.

Depending on the embodiment, each of the valves 160 can default to an open or closed position when the cassette 185 is not inserted into cavity 125 of the pump control unit 120. For example, in one embodiment, each of the valves 160 (such as valve 160-1, 160-2, and valve 160-3) is normally open prior to insertion of the cassette 185 in cavity 185. After cassette 185 is inserted in cavity 125, the pump controller unit 120 can adjust the default states to any desired open or closed settings.

The valve actuator resources in the pump controller unit 120 can control the respective valves 160 in any suitable manner depending on the type of the valves. For example, depending on the type of valves, via input from the pump control unit 120, the valves 160 can be electromechanically controlled, hydraulically controlled, pneumatically controlled, etc.

When the cassette 185 is loaded into the cavity 125 of the pump control unit 120, a respective actuator resource in the pump controller unit 120 engages to control each respective valve into a desired open or closed position. By way of a non-limiting example embodiment, as a safety feature, when the cassette 185 is first loaded into the cavity 125 of control unit 120, the actuator resources in the pump control unit 120 can be configured to control each of the valves 160-1, 160-2, and 160-3 to a closed position.

When pumping respective fluid from one or more fluid sources 189, the pump control unit 120 opens and closes valves 160.

For example, to draw fluid from the first fluid source 189-1 through the primary inlet 170-1 into pump chamber 110, the pump control unit 120 opens valve 160-1 and closes valve 160-2 and valve 160-3. While only valve 160-1 is open, the pump control unit 120 controls pump chamber actuator 193 to draw fluid through tube 165-1 into a pump chamber of fluid pump 110. After drawing sufficient amount of fluid into the pump chamber of fluid pump 110, the pump control unit 120 closes valves 160-1 and valve 160-2 and opens valve 160-3. While only valve 160-3 is open, the pump control unit 120 controls pump chamber actuator 193 to force the fluid in pump chamber 110 downstream along fluid pathway 115 through valve 160-3 to air elimination filter 140 in fluid pathway 115.

To draw fluid from the second fluid source 189-2 through the secondary inlet 170-2 into pump chamber 110, the pump control unit 120 opens valve 160-2 and closes valve 160-1 and valve 160-3. While only valve 160-2 is open, the pump control unit 120 controls pump chamber actuator 193 to draw fluid through tube 165-2 into pump chamber of fluid pump 110. After drawing sufficient amount of fluid into the pump chamber of fluid pump 110, the pump control unit 120 closes valves 160-1 and valve 160-2 and opens valve 160-3. While only valve 160-3 is open, the pump control unit 120 controls pump chamber actuator 193 to force the fluid in pump chamber of fluid pump 110 downstream along fluid pathway 115 through valve 160-3 to air elimination filter 140.

Embodiments herein can include switching between drawing fluids from the different fluid sources 189 and delivering such fluids to the recipient 182. For example, in a first pump cycle, the pump controller unit 120 can be configured to control valves to deliver fluid from fluid source 189-1 to recipient 182 in a manner as previously discussed; in a second pump cycle, the pump controller unit 120 can be configured to control valves to deliver fluid from fluid source 189-2 to recipient in a manner as previously discussed; in a third pump cycle, the pump controller unit 120 can be configured to control valves to deliver fluid from fluid source 189-1 to recipient 182 in a manner as previously discussed; in a fourth pump cycle, the pump controller unit 120 can be configured to control valves to deliver fluid from fluid source 189-2 to recipient in a manner as previously discussed; and so on. Accordingly, a single pump chamber 110 (such as diaphragm pump) in cassette 185 can be used to deliver fluid from different sources to a recipient 182.

Cassette 185 can further include air elimination filter 140 disposed downstream with respect to valve 160-3 in fluid pathway 115.

In one embodiment, the air elimination filter 140 is disposed upstream with respect to fluid flow resistor 145. Disposing the air elimination filter 140 upstream with respect to the fluid flow resistor 145 ensures that the air elimination filter 145 remains under positive pressure (e.g., a higher pressure than a pressure at a location monitored by pressure sensor 150 as discussed below) during fluid delivery.

As its name suggests, and as previously discussed, the air elimination filter 140 disposed in cassette 185 removes any air or gases from the fluid traveling downstream along fluid pathway 115 towards fluid flow resistor 145. In one embodiment, the air is vented out of the fluid pathway 115 into open air.

Fluid resistor drive 195 controls a degree to which the fluid flow resistor 145 resists a corresponding flow of the fluid along fluid pathway 115 towards recipient 182. In a similar manner as previously discussed, the fluid flow resistor 145 can be controlled in any suitable manner such as electromechanically controlled, hydraulically controlled, pneumatically controlled, etc.

Cassette 185 further includes pressure sensor 150 disposed downstream with respect to fluid flow resistor 145. In one non-limiting example embodiment, the pressure sensor 150 monitors a pressure of fluid disposed and passing through the location of fluid pathway 115 as shown. Via pressure sensor circuitry 196 in communication with pressure sensor 150, the pump control unit 120 is able to determine a pressure of fluid delivered to the recipient 182 at a downstream location in fluid pathway 115 with respect to the fluid flow resistor 145.

In one embodiment, the pressure sensor circuitry 196 detects when there is a blockage downstream preventing delivery of corresponding fluid to a recipient 182. For example, in one embodiment, when the pressure sensor circuitry 196 detects that the pressure at the location monitored by pressure sensor 150 is above a threshold value, the pressure sensor circuitry 196 generates a corresponding signal indicating a blockage and/or inability to deliver fluid to the recipient 182. Detecting pressure below the threshold value generally indicates that there is no blockage downstream and that the fluid is being delivered to the recipient 182.

Further, as previously discussed, note that the cassette 185 can include opening 135-1 and opening 135-2. Bubble detector element 130-1 protrudes through or into opening 135-1; bubble detector element 130-2 protrudes through or into opening 135-2. Bubble detector circuitry 172 monitors signals received from one or more elements 130-1 and 130-2.

During pumping of fluid to recipient 182, air elimination filter 140 removes gas from the infusion line (fluid pathway 115) before it reaches the elements 130. If the air elimination filter 140 fails and bubbles are detected by one or more detector elements 130-1 and 130-2, the bubble detector circuitry 172 generates a corresponding signal to pump control unit 120 to discontinue delivery of corresponding fluid to the recipient 182. This prevents any gas in the fluid being from being delivered to recipient 182 in the event that the air elimination filter 140 happens to fail to remove gas.

By way of non-limiting example, in one embodiment, in response to receiving an indication that bubbles are detected in fluid being delivered to the corresponding recipient 182, the pump control unit 120 can be configured to close valve 160-3 and/or deactivate fluid pump 110 to discontinue delivery of fluid to the recipient.

Thus, embodiments herein can include a disposable cassette 185 including fluid pathway 115. The fluid pathway 115 includes air elimination filter 140 and a flow resistor 145. The air elimination filter 140 is disposed in the fluid pathway 115 downstream of the fluid pump 110. The flow resistor 145 is disposed in the fluid pathway 115 downstream from the air elimination filter 140. As previously discussed, further embodiments herein include a pressure sensor 150. In the example embodiment shown, the fluid pathway 115 includes pressure sensor 150. Pressure sensor 150 monitors a pressure of fluid in the fluid pathway 115 at a location in the fluid pathway between the flow resistor 145 and the portion of the fluid pathway 115 between the first detector element 130-1 and second detector element 130-2.

Empty Source Container:

One common problem that exists with all infusions is that it is difficult to monitor and determine when the fluid container becomes empty, necessitating a change of container. When the fluid container is emptied, the flow rate is typically reduced from the flow rate prescribed by a physician to a "keep vein open" or KVO rate. If the empty or nearly empty container is not replaced or replenished the infusion pump will stop flow completely and the site can clot and otherwise become unusable. If the caregiver is not available to address the situation, a new infusion site may need to be found for subsequent infusions. This adds risk of infection, potentially causing harm to the patient.

In the case of "secondary" infusion, a fluid container containing a different IV (Intravenous) solution is attached to the source-side primary fluid line and its fluid is infused temporarily in lieu of the primary fluid until the secondary container is empty. During these infusions, attention must be given to the secondary fluid container so that air does not enter into the infusion line, cause an alarm, and stop the fluid flow.

One method used to monitor the state of the fluid container has been to estimate the volume of fluid in the secondary container and program the secondary mode of the pump to deliver this volume. This method is prone to errors due to mistakes or inaccurate estimations of the fluid infusion rate or the amount of fluid remaining in the container. Furthermore, there is a high degree of variability in actual amount of the fluid in an IV bag. The actual volume can vary by more than 10% from the specified value. The user is constantly making tradeoffs between trying to deliver the entire contents of the fluid source, without ending up with air in the flow path or wasting fluids.

The ability to deliver the entire contents of a bag to a patient, detect when the fluid source is empty, and then automatically purge air before alarming greatly reduces the work load on the caregiver and improves patient safety.

Secondary Infusion Automation:

Another benefit of the integrated air vent and air detection scheme in the pump is the simplification of preparing a secondary infusion. Presently, when the caregiver is preparing a secondary infusion, in addition to setting the bag at the correct height, the caregiver must completely purge all of the air from all of the source lines prior to connecting the line to the primary flow path. Furthermore the secondary infusion source container must be hung substantially higher than the primary fluid source. The preparation of this configuration is error prone, time consuming and can delay therapy.

Embodiments herein improve this workflow by not requiring the manual purging of air. According to embodiments herein, the secondary source container such as fluid source 189-2 and corresponding tube 165-3 can be connected to the disposable cassette 185 with air in the line.

When the secondary infusion (such as delivery of fluid from fluid source 189-2 to the recipient 182) starts, the fluid pump 110 simply starts pumping. The air (such as gas) in the fluid pathway 115 is automatically purged by a vent in the inline air elimination filter 140. When liquid is detected, the infused volume counter starts.

In many cases where secondary infusion is performed, the desired rate of secondary fluid flow is different from the desired rate of primary fluid flow. In this case, the operator must program the infusion pump (pump controller 120) with the estimated volume in the secondary fluid source 189-2, so that when the fluid pump 110 has infused that amount at the prescribed secondary rate, the pump will automatically transition to the primary flow rate. However, frequent errors due to incorrect estimation of container volume or inaccurate setting of the secondary volume-to-be-infused renders this method unreliable, requiring frequent monitoring by care-givers to ensure that the proper fluid is being infused at the proper rate, and to prevent air from entering into the infusion line and stopping flow.

What is needed is an inexpensive and reliable system and method for detecting when an infusion container is empty and method for providing a signal to an infusion pump to either alter the infusion rate, provide an alert signal to a caregiver that the container needs replenishment or replacement, or switch to a different infusion source. What is further needed is a reliable system and method for use with automatic secondary infusion setups that provide detection of the occurrence of transition from flow of the secondary fluid to flow of the primary fluid. Embodiments herein satisfy these needs.

Transportation:

Another common problem for caregivers delivering infusion treatments is disruption in fluid delivery flow due to presence of error that occurs from movement of the patient and or fluid delivery system. For example, during movement of the patient or equipment, small amounts of air can be introduced into the line (fluid pathway 115). Most infusion pump systems detect the air in line, alarm and stop the infusion. The patient is protected from air embolism but it creates additional work for the caregiver and could delay therapy. As previously discussed, embodiments herein purge air automatically from the inlet tubing during transport, enabling delivery of fluid to continue without the need to prompt the caregiver to replace the disposable tube set.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A fluid delivery system comprising:
    a fluid delivery assembly including an inlet, an outlet, a pneumatic pump, a fluid flow resistor, and a fluid pathway, the fluid pathway extending between the inlet and the outlet, the fluid flow resistor disposed in the fluid pathway, the pneumatic pump being a diaphragm pump;
    a pressure sensor to monitor a pressure of gas applied to a pumping chamber of the pneumatic pump, application of the pressure causing the diaphragm pump to pump fluid through the fluid pathway from the inlet to the outlet;
    a controller to control a flow rate of the fluid through the fluid pathway, the controller operable to control the pressure of the gas and control a setting of the fluid flow resistor, the controller operable to adjust the setting of the fluid flow resistor to deliver the fluid through the fluid pathway out of the outlet to a recipient, the fluid flow resistor incrementally adjustable by the controller in a range between a full open setting and a full closed setting to control the flow rate as indicated by a received flow rate setting, incremental adjustment of the setting of the fluid flow resistor by the controller operable to produce a corresponding incremental adjustment to the flow rate;
    the controller further operable to determine changes to the pressure of the gas and apply the changes to the pressure of the gas to control the flow rate of the fluid through the fluid pathway;
    wherein the flow rate of the fluid through the fluid pathway is calculated by: measuring the pressure of the gas applied to the pumping chamber of the diaphragm pump, measuring pressure of gas in a chamber of known volume, and then calculating a respective volume of the pumping chamber of the diaphragm pump over time based on the pressure of the gas applied to the pumping chamber and the known volume; and
    wherein the changes to the pressure represent an adjustment applied to the setting of the pressure of the gas in order to match the flow rate of the fluid through the fluid pathway to the received flow rate setting.

2. The fluid delivery system as in claim 1, wherein the controller operates the pneumatic pump to provide a continuous flow of the fluid in a flow range between one tenth of a milliliter per hour and one thousand milliliters per hour.

3. The fluid delivery system as in claim 1, wherein the fluid delivery assembly is a disposable cassette inserted into a cavity of the controller.

4. The fluid delivery system as in claim 1, wherein the fluid delivery assembly is a detachable and disposable with respect to the controller.

5. The fluid delivery system as in claim 1, wherein the fluid delivery assembly is disposable with respect to the controller and includes a bubble detector integrated into a cavity of the controller.

6. The fluid delivery system as in claim 5, wherein insertion of the fluid delivery assembly into the cavity aligns a portion of the fluid pathway in the cassette to be adjacent to the bubble detector.

7. The fluid delivery system as in claim 5, wherein the bubble detector includes a first element spaced apart from a second element;
    wherein the fluid delivery assembly includes a first opening to receive the first element; and
    wherein the fluid delivery assembly includes a second opening to receive the second element.

8. The fluid delivery system as in claim 7, wherein the first element and the second element protrude from a surface of the controller; and
    wherein a portion of the fluid pathway resides between the first element and the second element.

9. The fluid delivery system as in claim 5, wherein insertion of the fluid delivery assembly in the cavity aligns a portion of the fluid pathway adjacent to the bubble detector.

10. The fluid delivery system as in claim 1, wherein the controller monitors a pressure of fluid in the fluid pathway at a location in the fluid pathway between the fluid flow resistor and a bubble detector in the fluid delivery assembly.

11. The fluid delivery system as in claim 1, wherein the controller dynamically controls the setting of the fluid flow resistor to control the flow rate of the fluid through the fluid pathway.

12. The fluid delivery system as in claim 1, wherein the controller periodically calculates, based on a pressure of the gas as detected by the pressure sensor, a volume of fluid entering and leaving a chamber of the pneumatic pump over time to dynamically control the flow rate of the fluid through the fluid pathway.

13. The fluid delivery system as in claim 1, wherein the controller controls the pressure of the gas inputted to a chamber of the pneumatic pump to compensate for changes in a height of a source providing the fluid to the inlet.

14. The fluid delivery system as in claim 13, wherein the controller controls the pressure of the gas inputted to a chamber of the pneumatic pump to compensate for changes in fluid back pressure present on the outlet.

15. The fluid delivery system as in claim 4, wherein the controller operates the pneumatic pump to provide a continuous flow of fluid in a flow range between 0.1 milliliter per hour and one thousand milliliters per hour.

16. The system as in claim 1, wherein the pneumatic pump includes a chamber to receive the gas; and
wherein the controller determines the flow rate of the fluid out the outlet based on measuring an initial volume of the gas in the chamber of the pneumatic pump and then monitoring pressure decay of the volume of the gas in the chamber of the pneumatic pump over time.

17. The fluid delivery system as in claim 1, wherein the received flow rate setting is a non-zero flow rate setting of continuous fluid flow through the fluid flow resistor; and
wherein the controller, in addition to being operable to adjust the setting of the fluid flow resistor, is operable to control a magnitude of the pressure of the gas applied to operate the pneumatic pump to control the flow rate in accordance with the received flow rate setting.

18. The fluid delivery system as in claim 17, wherein the controller is operable to repeatedly adjust an orifice setting of the fluid flow resistor to fall between the full open setting and the full closed setting to deliver the fluid at a flow rate as indicated by the received flow rate setting.

19. The fluid delivery system as in claim 1, wherein the received flow rate setting indicates a respective flow rate that falls in a range between a non-zero minimum flow rate setting and a non-zero maximum flow rate setting.

20. The fluid delivery system as in claim 19, wherein the controller is operable to sense a flow rate of the fluid through the pathway; and
wherein the controller is operable to vary adjustment of the setting of the fluid flow resistor to be between the full open setting and the full closed setting in order to match the sensed flow rate of the fluid through the pathway to the received flow rate setting.

21. The fluid delivery system as in claim 20, wherein the controller is operable to control a pressure of the pneumatic pump and controls the setting of the fluid flow resistor to provide a continuous flow of the fluid to a recipient through the fluid pathway at the received flow rate setting.

22. The fluid delivery system as in claim 1, wherein the controller is operable to adjust the setting of the fluid flow resistor to be at an intermediate position in a range between the full open setting and the full closed setting to continuously deliver the fluid to the recipient as indicated by the received flow rate setting.

23. The fluid delivery system as in claim 22, wherein the controller is operable to vary the setting of the fluid flow resistor at intermediate positions in the range to selectively increase or decrease the flow rate of continuously delivering the fluid to the recipient.

24. The fluid delivery system as in claim 1, wherein the pressure sensor is a first pressure sensor, the fluid delivery system further comprising:
a second pressure sensor to detect a respective pressure of fluid in the fluid pathway between the fluid flow resistor and the outlet.

25. The fluid delivery system as in claim 1, wherein the fluid delivery system includes a cavity in which to receive the fluid delivery assembly.

26. The fluid delivery system as in claim 1, wherein the fluid delivery system includes a cavity in which to receive the fluid delivery assembly, the fluid delivery system further comprising:
a pneumatic interface disposed in the cavity, the pneumatic interface operable to guide and sealably couple a port on the fluid delivery assembly to the pneumatic interface when the fluid delivery assembly is inserted into the cavity, the pneumatic interface further operable to control the pneumatic pump and delivery of the fluid through the fluid pathway from the inlet to the outlet.

27. The fluid delivery system as in claim 26 further comprising:
a fluid resistor driver interface disposed in the cavity, the fluid resistor driver interface controlled by the controller to control the setting of the fluid flow resistor to multiple different positions in the range between the full open setting and the full closed setting of the fluid flow resistor to control the flow rate of the fluid through the fluid pathway.

28. The fluid delivery system as in claim 27, wherein the pneumatic pump includes a first chamber and a second chamber separated by a flexible membrane, the first chamber filled with a portion of the fluid passing through the fluid pathway, the second chamber filled with a portion of the gas; and
wherein the pressure sensor is disposed in the fluid delivery system external to the fluid delivery assembly.

29. The fluid delivery system as in claim 26, wherein the port of the fluid delivery assembly includes a protrusion; and
wherein the pneumatic interface includes an opening in the cavity to receive the protrusion.

30. The fluid delivery system as in claim 1, wherein the fluid delivery assembly includes multiple valves disposed in the pathway in addition to the fluid flow resistor, the fluid delivery system further comprising:
a control interface operable to control settings of the multiple valves and delivery of the fluid through the fluid pathway.

31. The fluid delivery system as in claim 1 further comprising:
a driver resource in communication with the fluid flow resistor, the driver resource operable to control a degree to which the fluid flow resistor resists the flow of the fluid through the fluid pathway.

32. The fluid delivery system as in claim 24, wherein the fluid delivery assembly is a disposable cassette removably inserted into a cavity of the fluid delivery system, the second pressure sensor disposed in the disposable cassette.

33. The fluid delivery system as in claim 1, wherein the controller is operable to calculate a flow rate of the fluid through the pathway; and wherein the controller is operable to modify the setting of the fluid flow resistor to a new setting between the full open setting and the full closed setting in order to control the flow rate of the fluid through the pathway to a desired flow rate setting inputted to the fluid delivery system.

34. The fluid delivery system as in claim 1, wherein application of the changes to the pressure of the gas is operable to control the flow rate of the fluid through the fluid pathway to the received flow rate setting.

35. The fluid delivery system as in claim 1, further comprising:

a flow control valve, the flow control valve disposed in the fluid pathway between the pneumatic pump and the fluid flow resistor, the controller operable to control a setting of the flow control valve to selectively control the flow of the fluid through the fluid flow resistor to a target recipient.

36. The fluid delivery system as in claim 35, wherein the fluid flow resistor is controlled independently with respect to the flow control valve.

37. The fluid delivery system as in claim 1 further comprising:

a flow control valve, the flow control valve disposed in the fluid pathway between the pneumatic pump and the fluid flow resistor, the controller operable to control a setting of the flow control valve to selectively prevent the flow of the fluid through the fluid flow resistor to a target recipient.

38. The fluid delivery system as in claim 37, wherein the controller is further operable to control the setting of the flow resistor independently of controlling the setting of the flow control valve.

39. The fluid delivery system as in claim 1, wherein the controller is operable to control a timing of applying changes to the pressure of the gas to control the flow rate of the fluid through the fluid pathway as indicated by the received flow rate setting.

40. The fluid delivery system as in claim 1 further comprising:

an air elimination filter disposed in the fluid pathway, the air elimination filter operable to remove air from the fluid passing through the fluid pathway; and wherein the fluid flows in a downstream direction through the fluid pathway from the inlet port to the outlet port, the air elimination filter disposed downstream in the fluid pathway with respect to the pneumatic pump, the fluid flow resistor disposed downstream in the fluid pathway with respect to the air elimination filter.

41. The fluid delivery system as in claim 1, wherein the controller is further operable to:

determine changes to the setting of the fluid flow resistor needed to match the flow rate of the fluid through the fluid pathway to the flow rate setting; and apply a combination of the changes to the pressure of the gas and the changes to the setting of the fluid flow resistor to match the flow rate of the fluid through the fluid pathway to the received flow rate setting.

42. The fluid delivery system as in claim 1, wherein the changes represent an adjustment needed to be applied to the setting of the pressure of the gas in order to subsequently match the flow rate of the fluid through the fluid pathway to the received flow rate setting.

43. The fluid delivery system as in claim 42, wherein the flow rate of the fluid through the fluid pathway is measured by periodically calculating the respective volume of the pumping chamber of the diaphragm pump over time.

44. The fluid delivery system as in claim 43, wherein the controller is operable to determine the respective volume based at least in part on the pressure of the gas applied to operate the pneumatic pump.

45. The fluid delivery system as in claim 44, wherein application of the changes to the pressure of the gas causes the flow rate of the fluid to match the received flow rate setting.

46. The fluid delivery system as in claim 45, wherein the pressure sensor is a first pressure sensor, the fluid delivery system further comprising:

a second pressure sensor to detect a respective pressure of fluid in the fluid pathway between the fluid flow resistor and the outlet.

47. The fluid delivery system as in claim 46, wherein the controller is further operable to:

determine changes to the setting of the fluid flow resistor needed to match the flow rate of the fluid through the fluid pathway to the flow rate setting; and apply a combination of the changes to the pressure of the gas and the changes to the setting of the fluid flow resistor to match the flow rate of the fluid through the fluid pathway to the flow rate setting.

48. The fluid delivery system as in claim 1, wherein gas in the chamber of known volume is selectively isolated from the gas in the pumping chamber of the diaphragm pump via a valve.

* * * * *